United States Patent
Abajian et al.

(10) Patent No.: US 6,767,897 B2
(45) Date of Patent: Jul. 27, 2004

(54) THERAPEUTIC USES OF TRI-, TETRA-, PENTA-, AND POLYPEPTIDES

(75) Inventors: Henry B. Abajian, Hillsdale, NJ (US); Joseph J. Hlavka, Tuxedo Park, NY (US); John P. Feighner, La Jolla, CA (US)

(73) Assignee: Innapharma, Inc., Park Ridge, NJ (US)

( * ) Notice: Subject to any disclaimer, the term of this patent is extended or adjusted under 35 U.S.C. 154(b) by 0 days.

(21) Appl. No.: 10/122,246

(22) Filed: Apr. 11, 2002

(65) Prior Publication Data

US 2003/0176354 A1 Sep. 18, 2003

Related U.S. Application Data

(63) Continuation-in-part of application No. 09/625,103, filed on Jul. 25, 2000, now abandoned, which is a continuation-in-part of application No. 08/962,962, filed on Nov. 4, 1997, now Pat. No. 6,093,797, which is a continuation-in-part of application No. 08/432,651, filed on May 2, 1995, now Pat. No. 5,767,083, which is a continuation-in-part of application No. 08/238,089, filed on May 4, 1994, now Pat. No. 5,589,460.

(51) Int. Cl.[7] .............................. A61K 38/08; C07K 7/06

(52) U.S. Cl. ......................................... 514/17; 530/330
(58) Field of Search .................... 514/17, 18; 530/330, 530/331

(56) References Cited

U.S. PATENT DOCUMENTS

| | | | | | |
|---|---|---|---|---|---|
| 3,795,738 | A | * | 3/1974 | Plotnikoff | 514/19 |
| 5,395,823 | A | * | 3/1995 | Krstenansky | 514/12 |
| 5,589,460 | A | * | 12/1996 | Abajian et al. | 514/17 |
| 5,767,083 | A | * | 6/1998 | Abajian et al. | 514/16 |
| 6,093,797 | A | * | 7/2000 | Abajian et al. | 530/329 |

* cited by examiner

*Primary Examiner*—Jeffrey Edwin Russel
(74) *Attorney, Agent, or Firm*—Duane Morris LLP

(57) ABSTRACT

Novel uses of certain peptides to treat patients suffering from neurological or psychiatric disorders are disclosed. The peptides include the tripeptide hormone MIF and compounds made by modifications of MIF, such as modification of amino terminus residues, carboxyl terminus residues and internal residues, including addition and substitution of amino acid residues and modification of the peptide bonds and functional side groups of respective amino acid residues. The tri-, tetra-, penta-, peptides and polypeptides may be utilized alone or in combination with other agents, to treat patients suffering from physiological, psychosomatic, neurological or psychiatric disorders.

6 Claims, No Drawings

SEQUENCE LISTING

```
<160> NUMBER OF SEQ ID NOS: 110

<210> SEQ ID NO 1
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: AMIDATION

<400> SEQUENCE: 1

Pro Leu Gly Trp
1
```

```
<210> SEQ ID NO 2
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: AMIDATION

<400> SEQUENCE: 2

Pro Ile Gly Trp
1

<210> SEQ ID NO 3
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 3

Pro Ile Gly Trp
1

<210> SEQ ID NO 4
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 3,4-dehydro-proline
<220> FEATURE:
<221> NAME/KEY: MOD_RES
<222> LOCATION: (4)..(4)
<223> OTHER INFORMATION: AMIDATION

<400> SEQUENCE: 4

Pro Ile Gly Trp
1

<210> SEQ ID NO 5
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 5

Pro Leu Gly Trp
1

<210> SEQ ID NO 6
```

```
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 6

Pro Leu Gly Tyr
1

<210> SEQ ID NO 7
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 7

Pro Arg Gly Trp
1

<210> SEQ ID NO 8
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 8

Pro Trp Gly Trp
1

<210> SEQ ID NO 9
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 9

Pro Ile Gly Tyr
1

<210> SEQ ID NO 10
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 10
```

Trp Pro Leu Gly
1

<210> SEQ ID NO 11
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 11

Phe Pro Leu Gly
1

<210> SEQ ID NO 12
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (4)..(4)
<223> OTHER INFORMATION: AMIDATION

<400> SEQUENCE: 12

Phe Pro Leu Gly
1

<210> SEQ ID NO 13
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-chlorophenylalanine
<220> FEATURE:
<221> NAME/KEY: MOD_RES
<222> LOCATION: (4)..(4)
<223> OTHER INFORMATION: AMIDATION

<400> SEQUENCE: 13

Phe Pro Leu Gly
1

<210> SEQ ID NO 14
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (4)..(4)
<223> OTHER INFORMATION: AMIDATION

```
<400> SEQUENCE: 14

Phe Pro Ile Gly
1

<210> SEQ ID NO 15
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (4)..(4)
<223> OTHER INFORMATION: AMIDATION

<400> SEQUENCE: 15

Phe Pro Leu Gly
1

<210> SEQ ID NO 16
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (4)..(4)
<223> OTHER INFORMATION: AMIDATION

<400> SEQUENCE: 16

Phe Pro Ile Gly
1

<210> SEQ ID NO 17
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 17

Trp Pro Leu Gly
1

<210> SEQ ID NO 18
<211> LENGTH: 4
<212> TYPE: PRT
<213> ORGANISM: Artificial
<220> FEATURE:
<223> OTHER INFORMATION: Synthetic Peptide
```

```
<220> FEATURE:
<221> NAME/KEY: MOD_RES
<222> LOCATION: (4)..(4)
<223> OTHER INFORMATION: AMIDATION

<400> SEQUENCE: 18

Trp Pro Ile Gly
1

<210> SEQ ID NO 19
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (4)..(4)
<223> OTHER INFORMATION: AMIDATION

<400> SEQUENCE: 19

Trp Pro Leu Gly
1

<210> SEQ ID NO 20
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (4)..(4)
<223> OTHER INFORMATION: AMIDATION

<400> SEQUENCE: 20

Trp Pro Ile Gly
1

<210> SEQ ID NO 21
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (5)..(5)
<223> OTHER INFORMATION: AMIDATION

<400> SEQUENCE: 21

Phe Tyr Pro Leu Gly
1               5

<210> SEQ ID NO 22
<211> LENGTH: 5
<212> TYPE: PRT
<213> ORGANISM: Artificial
<220> FEATURE:
```

```
<223> OTHER INFORMATION: Synthetic Peptide
<220> FEATURE:
<221> NAME/KEY: MOD_RES
<222> LOCATION: (1)..(1)
<223> OTHER INFORMATION: 4-chlorophenylalanine
<220> FEATURE:
<221> NAME/KEY: MOD_RES
<222> LOCATION: (5)..(5)
<223> OTHER INFORMATION: AMIDATION

<400> SEQUENCE: 22

Phe Tyr Pro Leu Gly
1               5

<210> SEQ ID NO 23
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 23

Phe Tyr Pro Leu Gly
1               5

<210> SEQ ID NO 24
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 24

Phe Tyr Pro Ile Gly
1               5

<210> SEQ ID NO 25
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 25

Phe Tyr Pro Leu Gly
1               5

<210> SEQ ID NO 26
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
```

```
<222> LOCATION: (3)..(3)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 26

Phe Tyr Pro Ile Gly
1               5

<210> SEQ ID NO 27
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 27

Tyr Tyr Pro Leu Gly
1               5

<210> SEQ ID NO 28
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 28

Tyr Tyr Pro Ile Gly
1               5

<210> SEQ ID NO 29
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 29

Tyr Tyr Pro Leu Gly
1               5

<210> SEQ ID NO 30
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: 4Hyp
<220> FEATURE:
```

```
<221> NAME/KEY: MOD_RES
<222> LOCATION: (5)..(5)
<223> OTHER INFORMATION: AMIDATION

<400> SEQUENCE: 30

Tyr Tyr Pro Ile Gly
1               5

<210> SEQ ID NO 31
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 31

Phe Pro Leu Gly Trp
1               5

<210> SEQ ID NO 32
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 32

Tyr Pro Leu Gly Trp
1               5

<210> SEQ ID NO 33
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 33

Phe Pro Leu Gly Trp
1               5

<210> SEQ ID NO 34
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 34

Phe Pro Ile Gly Trp
```

```
<210> SEQ ID NO 35
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 35

Phe Pro Ile Gly Trp
1               5

<210> SEQ ID NO 36
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 36

Tyr Pro Leu Gly Trp
1               5

<210> SEQ ID NO 37
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 37

Tyr Pro Ile Gly Trp
1               5

<210> SEQ ID NO 38
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 38
```

```
Tyr Pro Leu Gly Trp
1               5

<210> SEQ ID NO 39
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 39

Tyr Pro Trp Gly Trp
1               5

<210> SEQ ID NO 40
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 40

Tyr Pro Trp Gly Trp
1               5

<210> SEQ ID NO 41
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 41

Phe Pro Ile Gly Trp
1               5

<210> SEQ ID NO 42
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
```

```
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 42

Phe Pro Leu Gly Trp
1               5

<210> SEQ ID NO 43
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 43

Phe Pro Arg Gly Trp
1               5

<210> SEQ ID NO 44
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 44

Pro Ile Leu Gly Trp
1               5

<210> SEQ ID NO 45
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 45

Pro Ile Leu Gly Trp
1               5

<210> SEQ ID NO 46
<211> LENGTH: 6
<212> TYPE: PRT
```

```
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (6)..(6)
<223> OTHER INFORMATION: AMIDATION

<400> SEQUENCE: 46

Phe Pro Ile Gly Trp Gly
1               5

<210> SEQ ID NO 47
<211> LENGTH: 7
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (7)..(7)
<223> OTHER INFORMATION: AMIDATION

<400> SEQUENCE: 47

Phe Pro Ile Gly Trp Gly Trp
1               5

<210> SEQ ID NO 48
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (6)..(6)
<223> OTHER INFORMATION: AMIDATION

<400> SEQUENCE: 48

Phe Pro Leu Gly Trp Gly
1               5

<210> SEQ ID NO 49
<211> LENGTH: 7
<212> TYPE: PRT
<213> ORGANISM: Artificial
<220> FEATURE:
<223> OTHER INFORMATION: Synthetic Peptide
<220> FEATURE:
```

```
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (7)..(7)
<223> OTHER INFORMATION: AMIDATION

<400> SEQUENCE: 49

Phe Pro Leu Gly Trp Gly Trp
1               5

<210> SEQ ID NO 50
<211> LENGTH: 7
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: AMIDATION

<400> SEQUENCE: 50

Pro Ile Gly Trp Pro Ile Gly
1               5

<210> SEQ ID NO 51
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (6)..(6)
<223> OTHER INFORMATION: AMIDATION

<400> SEQUENCE: 51

Phe Pro Arg Gly Trp Gly
1               5

<210> SEQ ID NO 52
<211> LENGTH: 7
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (7)..(7)
<223> OTHER INFORMATION: AMIDATION
```

```
<400> SEQUENCE: 52

Phe Pro Arg Gly Trp Gly Trp
1               5

<210> SEQ ID NO 53
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4Hyp
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (6)..(6)
<223> OTHER INFORMATION: AMIDATION

<400> SEQUENCE: 53

Pro Ile Gly Pro Ile Gly
1               5

<210> SEQ ID NO 54
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 54

Tyr Pro Trp Gly
1

<210> SEQ ID NO 55
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: AMIDATION

<400> SEQUENCE: 55

Phe Pro Arg Gly Trp
1               5

<210> SEQ ID NO 56
<211> LENGTH: 7
<212> TYPE: PRT
<213> ORGANISM: Artificial
<220> FEATURE:
<223> OTHER INFORMATION: Synthetic Peptide
```

```
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (7)..(7)
<223> OTHER INFORMATION: AMIDATION

<400> SEQUENCE: 56

Phe Pro Arg Gly Ile Gly Trp
1               5

<210> SEQ ID NO 57
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: homo-proline
<220> FEATURE:
<221> NAME/KEY: MOD_RES
<222> LOCATION: (5)..(5)
<223> OTHER INFORMATION: AMIDATION

<400> SEQUENCE: 57

Phe Pro Arg Gly Trp
1               5

<210> SEQ ID NO 58
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (6)..(6)
<223> OTHER INFORMATION: AMIDATION

<400> SEQUENCE: 58

Phe Pro Arg Gly Gly Trp
1               5

<210> SEQ ID NO 59
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-methoxyphenylalanine
```

```
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 59

Phe Pro Arg Gly Trp
1               5

<210> SEQ ID NO 60
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-chlorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (4)..(4)
<223> OTHER INFORMATION: AMIDATION

<400> SEQUENCE: 60

Phe Pro Ile Gly
1

<210> SEQ ID NO 61
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-chlorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 61

Phe Pro Arg Gly Trp
1               5

<210> SEQ ID NO 62
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 3,4-dehydroproline
<220> FEATURE:
<221> NAME/KEY: MOD_RES
<222> LOCATION: (4)..(4)
<223> OTHER INFORMATION: AMIDATION
```

```
<400> SEQUENCE: 62

Pro Arg Gly Trp
1

<210> SEQ ID NO 63
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-aminophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 63

Phe Pro Arg Gly Trp
1               5

<210> SEQ ID NO 64
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 64

Phe Pro His Gly Trp
1               5

<210> SEQ ID NO 65
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-nitrophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 65

Phe Pro Arg Gly Trp
```

<210> SEQ ID NO 66
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 3-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 66

Phe Pro Arg Gly Trp
1               5

<210> SEQ ID NO 67
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (6)..(6)
<223> OTHER INFORMATION: AMIDATION

<400> SEQUENCE: 67

Phe Pro Arg Ile Gly Trp
1               5

<210> SEQ ID NO 68
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 2-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 68

Phe Pro Arg Gly Trp
1               5

<210> SEQ ID NO 69

```
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: homo-proline
<220> FEATURE:
<221> NAME/KEY: MOD_RES
<222> LOCATION: (5)..(5)
<223> OTHER INFORMATION: AMIDATION

<400> SEQUENCE: 69

Phe Pro Ile Gly Trp
1               5

<210> SEQ ID NO 70
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 3-(3-pyridyl)alanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 70

Ala Pro Arg Gly Trp
1               5

<210> SEQ ID NO 71
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (3)..(3)
<223> OTHER INFORMATION: homo-arginine
<220> FEATURE:
<221> NAME/KEY: MOD_RES
<222> LOCATION: (5)..(5)
<223> OTHER INFORMATION: AMIDATION

<400> SEQUENCE: 71

Phe Pro Arg Gly Trp
1               5

<210> SEQ ID NO 72
```

```
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: AMIDATION

<400> SEQUENCE: 72

Phe Pro Ile Gly Trp
1               5

<210> SEQ ID NO 73
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (3)..(3)
<223> OTHER INFORMATION: L-allo-isoleucine
<220> FEATURE:
<221> NAME/KEY: MOD_RES
<222> LOCATION: (5)..(5)
<223> OTHER INFORMATION: AMIDATION

<400> SEQUENCE: 73

Phe Pro Ile Gly Trp
1               5

<210> SEQ ID NO 74
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (3)..(3)
<223> OTHER INFORMATION: homo-arginine

<400> SEQUENCE: 74

Phe Pro Arg Gly Trp
1               5

<210> SEQ ID NO 75
```

```
<211> LENGTH: 4
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (4)..(4)
<223> OTHER INFORMATION: glycine-1,2,3,4-tetrahydroisoquinoline-3-
      carboxamide

<400> SEQUENCE: 75

Phe Pro Arg Gly
1

<210> SEQ ID NO 76
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 3,4-dichlorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 76

Phe Pro Arg Gly Trp
1               5

<210> SEQ ID NO 77
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-cyanophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: AMIDATION

<400> SEQUENCE: 77

Phe Pro Arg Gly Trp
1               5

<210> SEQ ID NO 78
<211> LENGTH: 5
<212> TYPE: PRT
<213> ORGANISM: Artificial
```

```
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (3)..(3)
<223> OTHER INFORMATION: D-leucine
<220> FEATURE:
<221> NAME/KEY: MOD_RES
<222> LOCATION: (5)..(5)
<223> OTHER INFORMATION: AMIDATION

<400> SEQUENCE: 78

Phe Pro Leu Gly Trp
1               5

<210> SEQ ID NO 79
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: trans-3-hydroxyproline
<220> FEATURE:
<221> NAME/KEY: MOD_RES
<222> LOCATION: (5)..(5)
<223> OTHER INFORMATION: AMIDATION

<400> SEQUENCE: 79

Phe Pro Arg Gly Trp
1               5

<210> SEQ ID NO 80
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (6)..(6)
<223> OTHER INFORMATION: AMIDATION

<400> SEQUENCE: 80

Phe Pro Arg Gly Gly Trp
1               5

<210> SEQ ID NO 81
<211> LENGTH: 5
<212> TYPE: PRT
<213> ORGANISM: Artificial
```

```
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-methoxyphenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: AMIDATION

<400> SEQUENCE: 81

Phe Pro Arg Gly Trp
1               5

<210> SEQ ID NO 82
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 2,4-difluorophenylalanine
<220> FEATURE:
<221> NAME/KEY: MOD_RES
<222> LOCATION: (2)..(2)
<223> OTHER INFORMATION: 3,4-dihydroproline
<220> FEATURE:
<221> NAME/KEY: MOD_RES
<222> LOCATION: (5)..(5)
<223> OTHER INFORMATION: AMIDATION

<400> SEQUENCE: 82

Phe Pro Arg Gly Trp
1               5

<210> SEQ ID NO 83
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-trifluoromethylphenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: AMIDATION

<400> SEQUENCE: 83

Phe Pro Arg Gly Trp
1               5

<210> SEQ ID NO 84
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
```

```
<222> LOCATION: (1)..(1)
<223> OTHER INFORMATION: 4-fluorophenylglycine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: AMIDATION

<400> SEQUENCE: 84

Gly Pro Arg Gly Trp
1               5

<210> SEQ ID NO 85
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 3-flurotyrosine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: AMIDATION

<400> SEQUENCE: 85

Tyr Pro Arg Gly Trp
1               5

<210> SEQ ID NO 86
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: carboxyl-terminal hydroxyamino group

<400> SEQUENCE: 86

Phe Pro Arg Gly Trp
1               5

<210> SEQ ID NO 87
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 3,4-dichlorophenylalanine
<220> FEATURE:
<221> NAME/KEY: MOD_RES
```

```
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: AMIDATION

<400> SEQUENCE: 87

Phe Pro Arg Gly Trp
1               5

<210> SEQ ID NO 88
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 2-fluorotyrosine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: AMIDATION

<400> SEQUENCE: 88

Tyr Pro Arg Gly Trp
1               5

<210> SEQ ID NO 89
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 7-azatryptophan, carboxyl-terminal amidated

<400> SEQUENCE: 89

Phe Pro Arg Gly Trp
1               5

<210> SEQ ID NO 90
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
```

```
<222> LOCATION: (5)..(5)
<223> OTHER INFORMATION: 4-fluorotryptophan, carboxyl-terminal amidated

<400> SEQUENCE: 90

Phe Pro Arg Gly Trp
1               5

<210> SEQ ID NO 91
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 5-fluorotryptophan, carboxyl-terminal amidated

<400> SEQUENCE: 91

Phe Pro Arg Gly Trp
1               5

<210> SEQ ID NO 92
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 6-fluorotryptophan, carboxyl-terminal amidated

<400> SEQUENCE: 92

Phe Pro Arg Gly Trp
1               5

<210> SEQ ID NO 93
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 3-methoxytryptophan, carboxyl-terminal amidated

<400> SEQUENCE: 93
```

```
Phe Pro Arg Gly Trp
1               5

<210> SEQ ID NO 94
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: N-methyltryptophan, carboxyl-terminal amidated

<400> SEQUENCE: 94

Phe Pro Arg Gly Trp
1               5

<210> SEQ ID NO 95
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 1-methyltryptophan, carboxyl-terminal amidated

<400> SEQUENCE: 95

Phe Pro Arg Gly Trp
1               5

<210> SEQ ID NO 96
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 4-methyltryptophan, carboxyl-terminal amidated

<400> SEQUENCE: 96

Phe Pro Arg Gly Trp
1               5
```

```
<210> SEQ ID NO 97
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 5-methyltryptophan, carboxyl-terminal amidated

<400> SEQUENCE: 97

Phe Pro Arg Gly Trp
1               5

<210> SEQ ID NO 98
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 6-methyltryptophan, carboxyl-terminal amidated

<400> SEQUENCE: 98

Phe Pro Arg Gly Trp
1               5

<210> SEQ ID NO 99
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: MOD_RES
<222> LOCATION: (5)..(5)
<223> OTHER INFORMATION: 5-hydroxytryptophan, carboxyl-terminal amidated

<400> SEQUENCE: 99

Phe Pro Arg Gly Trp
1               5

<210> SEQ ID NO 100
<211> LENGTH: 5
<212> TYPE: PRT
```

```
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: misc_feature
<222> LOCATION: (2)..(2)
<223> OTHER INFORMATION: isonipecotic acid residue
<220> FEATURE:
<221> NAME/KEY: MOD_RES
<222> LOCATION: (5)..(5)
<223> OTHER INFORMATION: AMIDATION

<400> SEQUENCE: 100

Phe Xaa Arg Gly Trp
1               5

<210> SEQ ID NO 101
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: misc_feature
<222> LOCATION: (2)..(2)
<223> OTHER INFORMATION: 2-carboxy-azetidine
<220> FEATURE:
<221> NAME/KEY: MOD_RES
<222> LOCATION: (5)..(5)
<223> OTHER INFORMATION: AMIDATION

<400> SEQUENCE: 101

Phe Xaa Arg Gly Trp
1               5

<210> SEQ ID NO 102
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: misc_feature
<222> LOCATION: (2)..(2)
<223> OTHER INFORMATION: 1-amino-1-carboxycyclopentane
<220> FEATURE:
<221> NAME/KEY: MOD_RES
<222> LOCATION: (5)..(5)
<223> OTHER INFORMATION: AMIDATION

<400> SEQUENCE: 102

Phe Xaa Arg Gly Trp
1               5

<210> SEQ ID NO 103
<211> LENGTH: 5
<212> TYPE: PRT
<213> ORGANISM: Artificial
<220> FEATURE:
<223> OTHER INFORMATION: Synthetic Peptide
<220> FEATURE:
```

```
<221> NAME/KEY: MOD_RES
<222> LOCATION: (1)..(1)
<223> OTHER INFORMATION: 4-fluorophenylalanine
<220> FEATURE:
<221> NAME/KEY: misc_feature
<222> LOCATION: (2)..(2)
<223> OTHER INFORMATION: 2-carboxy-aziridine
<220> FEATURE:
<221> NAME/KEY: MOD_RES
<222> LOCATION: (5)..(5)
<223> OTHER INFORMATION: AMIDATION

<400> SEQUENCE: 103

Phe Xaa Arg Gly Trp
1               5

<210> SEQ ID NO 104
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: misc_feature
<222> LOCATION: (2)..(2)
<223> OTHER INFORMATION: 1-amino-1-carboxy-cyclopropyl residue
<220> FEATURE:
<221> NAME/KEY: MOD_RES
<222> LOCATION: (5)..(5)
<223> OTHER INFORMATION: AMIDATION

<400> SEQUENCE: 104

Phe Xaa Arg Gly Trp
1               5

<210> SEQ ID NO 105
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: misc_feature
<222> LOCATION: (2)..(2)
<223> OTHER INFORMATION: 3-carboxy-1,4,5,6-tetrahydropyridine
<220> FEATURE:
<221> NAME/KEY: MOD_RES
<222> LOCATION: (5)..(5)
<223> OTHER INFORMATION: AMIDATION

<400> SEQUENCE: 105

Phe Xaa Arg Gly Trp
1               5

<210> SEQ ID NO 106
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
```

```
<221> NAME/KEY: misc_feature
<222> LOCATION: (2)..(2)
<223> OTHER INFORMATION: 2-carboxypyrrole
<220> FEATURE:
<221> NAME/KEY: MOD_RES
<222> LOCATION: (5)..(5)
<223> OTHER INFORMATION: AMIDATION

<400> SEQUENCE: 106

Phe Xaa Arg Gly Trp
1               5

<210> SEQ ID NO 107
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4-flurotryptophan, carboxyl-terminal amidated

<400> SEQUENCE: 107

Phe Pro Arg Gly Trp
1               5

<210> SEQ ID NO 108
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 7-methyltryptophan, carboxyl-terminal amidated

<400> SEQUENCE: 108

Phe Pro Arg Gly Trp
1               5

<210> SEQ ID NO 109
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 4Hyp
<220> FEATURE:
```

```
-continued

<221> NAME/KEY: MOD_RES
<222> LOCATION: (3)..(3)
<223> OTHER INFORMATION: 5,5,5-trifluoroleucine
<220> FEATURE:
<221> NAME/KEY: MOD_RES
<222> LOCATION: (5)..(5)
<223> OTHER INFORMATION: AMIDATION

<400> SEQUENCE: 109

Phe Pro Leu Gly Trp
1               5

<210> SEQ ID NO 110
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: 3,4-dehydroproline
<220> FEATURE:
<221> NAME/KEY: misc_feature
<222> LOCATION: (4)..(4)
<223> OTHER INFORMATION: Sarcosine
<220> FEATURE:
<221> NAME/KEY: MOD_RES
<222> LOCATION: (5)..(5)
<223> OTHER INFORMATION: AMIDATION

<400> SEQUENCE: 110

Phe Pro Arg Xaa Trp
1               5
```

THERAPEUTIC USES OF TRI-, TETRA-, PENTA-, AND POLYPEPTIDES

CROSS-REFERENCE TO RELATED APPLICATIONS

This application is a continuation-in-part of U.S. patent application Ser. No. 09/625,103 filed Jul. 25, 2000, abandoned, which is a continuation-in-part of U.S. patent application Ser. No. 08/962,962 filed Nov. 4, 1997, now U.S. Pat. No. 6,093,797, which is a continuation-in-part of U.S. patent application Ser. No. 08/432,651 filed on May 2, 1995, now U.S. Pat. No. 5,767,083, which is a continuation-in-part of U.S. patent application Ser. No. 08/238,089 filed on May 4, 1994, no U.S. Pat. No. 5,589,460. The disclosures of each of U.S. Pat. Nos. 6,093,797; 5,767,083; and 5,589,460 are hereby incorporated herein by reference in their entirety.

FIELD OF THE INVENTION

The present invention is related to methods for treating patients suffering from physiological, psychosomatic, neurological or psychiatric disorders. The methods include the administration of certain peptides.

BACKGROUND OF THE INVENTION

Endogenous depression is thought to be a genetically determined biochemical disorder which can result in an inability to deal with stress. Treatment for endogenous depression includes electroconvulsive therapy and/or drug therapy. Drugs administered for therapeutic treatment of depression include tricyclic antidepressants, monoamine oxidase (MAO) inhibitors, "second-generation" antidepressants, and selective serotonin reuptake inhibitors (SSRIs).

Tricyclic antidepressants (TPAs) have been the drug of first choice in treating endogenous depression for over three decades. However, these drugs have limited efficacy in that 40 to 60% of patients receiving tricyclic drugs do not respond favorably. The side effects of the tricyclics are numerous, including cholinergic blockage, cardiac complications, allergic reactions, dry mouth, constipation, blurred vision and tachycardia. Tricyclic antidepressants are characterized by a three-ringed structure, and include imipramine, desipramine, amitriptyline, nortriptyline, protriptyline, doxepin and trimipramine. The tricyclic antidepressants are metabolized through the mixed-function oxidase system, and the metabolites of the tricyclic antidepressants are also pharmacologically active compounds.

The MAO inhibitors have been available for treatment of depression since the 1950's. MAO inhibitors are classified either as hydrazides, which contain by a C—N—N moiety (e.g., phenelzine and isocarboxazide) or nonhydrazides (e.g., tranylcypromine). MAO inhibitors have not gained wide acceptance due to serious side effects.

The second-generation antidepressants include amoxapine, maprotiline, nefasodone, trazodone and bupropion. The second-generation antidepressants a produce a variety of effects on serotonergic and dopaminergic activity.

The selective serotonin reuptake inhibitors, including fluoxetine, sertraline, paroxetine, fluoroxamine, and citalopram, are believed to work primarily by a serotonergic mechanism. They are safer and better tolerated than the TCAs and MAOIs, but are probably not as effective in more serious depression and have troublesome side effects such as sexual dysfunction in about 40% of patients. In addition, about thirty percent of patients do not have a favorable response with the SSRIs.

The tripeptide MIF, otherwise known as melanocyte stimulating inhibitory factor, which is represented by the chemical formula of prolyl-leucyl-glycinamide or Pro-Leu-Gly-$NH_2$, has been shown to produce numerous non-endocrine effects on the brain. The MIF tripeptide has also been shown to be active in a number of animal models for depression.

A need remains for new and/or improved methods and compositions for treating psychiatric and neurological disorders. In particular, it is desired to provide such new methods and compositions while reducing and preferably minimizing undesired side effects.

SUMMARY OF THE INVENTION

The present invention provides compositions and methods for treating physiological, psychosomatic, neurological or psychiatric disorders. The compositions are peptides. The compositions and methods are useful in treating patients suffering from neurological or psychiatric disorders.

It has been found that peptides described herein are potentially useful in treating a variety of physiological, psychosomatic, neurological and psychological disorders, including bipolar disorder, seasonal affective disorder, eating disorders such as bulimia, anorexia nervosa and exogenous obesity, chronic fatigue syndrome, fibromyalgia, sexual dysfunction, anxiety disorders, attention deficit disorder, Parkinson's disease, depression accompanying schizophrenia, jet lag syndrome and addiction disorders including alcohol dependence. It has further been found that the methods and compositions disclosed herein are effective in treating depression in patients that are deemed unresponsive to conventional anti-depressant medications. Such patients may be referred to as "refractory" patients.

It has further been found that the methods and compositions disclosed herein are useful in treating patients suffering from anxiety. In treating patients suffering from anxiety, the compositions disclosed herein may be administered alone or in combination with other pharmaceutical compounds.

According to one aspect of the invention, there is provided a method for treating a patient suffering from bipolar disorder. The method comprises administering to the patient a pharmaceutically effective amount of one or more of the peptides disclosed herein.

According to another aspect of the invention, there is provided a method for treating a patient suffering from seasonal affective disorder. The method comprises administering to the patient a pharmaceutically effective amount of one or more of the peptides disclosed herein.

According to another aspect of the invention, there is provided a method for treating a patient suffering from an eating disorder. The method comprises administering to the patient a pharmaceutically effective amount of one or more of the peptides disclosed herein.

According to another aspect of the invention, there is provided a method for treating a patient suffering from fibromyalgia or chronic fatigue syndrome. The method comprises administering to the patient a pharmaceutically effective amount of one or more of the peptides disclosed herein.

According to another aspect of the invention, there is provided a method for treating a patient suffering from sexual dysfunction. The method comprises administering to the patient a pharmaceutically effective amount of one or more of the peptides disclosed herein.

According to one another aspect of the invention, there is provided a method for treating a patient suffering from anxiety disorder. The method comprises administering to the patient a pharmaceutically effective amount of one or more of the peptides disclosed herein.

According to another aspect of the invention, there is provided a method for treating a patient suffering from attention deficit disorder. The method comprises administering to the patient a pharmaceutically effective amount of one or more of the peptides disclosed herein.

According to another aspect of the invention, there is provided a method for treating a patient suffering from Parkinson's disease. The method comprises administering to the patient a pharmaceutically effective amount of one or more of the peptides disclosed herein.

According to another aspect of the invention, there is provided a method for treating a patient suffering from depression accompanying schizophrenia. The method comprises administering to the patient a pharmaceutically effective amount of one or more of the peptides disclosed herein.

Peptides for use in the methods described herein include compounds made by modifications, substitutions, additions and/or deletions to a MIF core structure, Pro-Leu-Gly-NH$_2$, also referred to herein as "modified MIF compounds". The modified MIF compounds have been found to have pharmacological activity and to be useful in treating a variety of neurological or psychiatric disorders.

The compounds disclosed herein may be administered by a variety of routes, including subcutaneously, intramuscularly, orally, sublingually, and transdermally.

DETAILED DESCRIPTION OF THE INVENTION

Preferred compositions for use in treating neurological or psychiatric disorders according to the methods described herein are peptides having selected modifications as compared to MIF. Modifications may be introduced, for example, at amino terminus residues, carboxyl terminus residues and/or internal residues. Exemplary modifications include addition and substitution of amino acid residues and modification of the peptide bonds and functional side groups of respective amino acid residues as more fully described hereinbelow.

Unless stated otherwise, the following terms and abbreviations when used herein have the meanings set forth below.

"Carboxyl" means any functional group having the formula —CO$_2$H or —RCO$_2$H, wherein R represents a monocyclic organic compound including a three to six member ring, of which at least one member is a nitrogen atom.

"Hydroxyalkyl" means any functional group having the formula —ROH, where R represents a lower alkyl group, preferably having 1 to 3 carbon atoms.

"Carbamyl" means any functional group having the formula —CONH$_2$ or —RCONH2, wherein R represents a heterocyclic organic compound including a ten member ring, of which at least one member is a nitrogen atom.

"Alkylcarbamyl" means any functional group having the formula CONR$^1$R$^2$ wherein R$^1$ and R$^2$ each independently represent a hydrogen atom or a lower alkyl group, preferably having 1 to 3 carbon atoms.

"Alkoxycarbonyl" means any functional group having the formula CO$_2$R, wherein R represents a lower alkyl group, preferably having 1 to 3 carbon atoms.

| | |
|---|---|
| dehydro | anhydro group where one or more hydrogen atoms are removed; |
| hydroxyl | alcohol group or —OH or —ROH where R represents a lower alkyl group, preferably having 1 to 3 carbon atoms; |
| sulphydryl | thiol group —SH or —RSH where R represents a lower alkyl group, preferably having 1 to 3 carbon atoms; |
| alkylamino | —NHR where R represents a lower alkyl group, preferably having 1 to 3 carbon atoms; |
| dialkylamino | —NR$_2$ where R represents a lower alkyl group, preferably having 1 to 3 carbon atoms; |
| hydroxyamino | —NHOH group; |
| patient | includes any member of the animal kingdom, including but not solely limited to humans; and, |
| CGI | Control group inactive. |
| Pro | L-proline; |
| Leu | L-leucine; |
| Gly | L-glycine; |
| Tyr | L-tyrosine; |
| Ala | L-alanine; |
| Arg | L-arginine; |
| Lys | L-lysine; |
| Phe | L-phenylalanine; |
| Trp | L-tryptophan; |
| Ile | L-isoleucine; |
| Orn | L-ornithine; |
| D-Arg | D-arginine; |
| D-Leu | D-leucine; |
| 3,4-dehydro-Pro | 3,4-dehydro-L-proline; |
| pGlu | pyro-glutamic acid; |
| Sar | L-sarcosine (N-methylglycine); |
| 4-OH-Pro | 4-hydroxyproline; |
| 4-thio-Pro | 4-thioproline; |
| 2-F-Phe | 2-fluorophenylalanine; |
| 3-F-Phe | 3-fluorophenylalanine; |
| 4-F-Phe | 4-fluorophenylalanine; |
| 4-Cl-Phe | 4-chlorophenylalanine; |
| 4-NH$_2$-Phe | 4-aminophenylalanine; |
| 3(3-pyridyl)Ala | 3(3-pyridyl)-alanine |
| Homo-Arg | Homo-arginine |
| Homo-Pro | Homo-proline |
| Fmoc | 9-Fluorenylmethoxycarbonyl; |
| TFA | trifluoroacetic acid; |

One embodiment of the peptides of the present invention includes tripeptides characterized by formula (1):

$$R^1\text{-Pro}^1\text{-AA}^1\text{-NR}^2\text{—CH}_2\text{—R} \tag{1}$$

where Pro$^1$ represents the amino acid Pro or dehydro-Pro, preferably 3,4-dehydro Pro; AA$^1$ represents an amino acid of the group Trp, Orn, Lys, Leu, D-Leu, Arg, D-Arg, or Ile; R represents a carboxyl group, a hydroxyalkyl group, a carbamyl group, an alkylcarbamyl group, or an alkoxycarbonyl group; R$^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino group or dimethyl or diethylamino group; and, R$^2$ represents a hydrogen atom or a lower alkyl group, preferably having 1 to 3 carbon atoms, with the proviso that where Pro$^1$ is Pro and AA$^1$ is Leu, then R$^1$ and R$^2$ are not both hydrogen atoms when R is a carbamyl group.

An embodiment of peptides of formula (1) useful in the treatment methods described herein is a tripeptide having formula (1a):

$$\text{Pro}^1\text{-AA}^1\text{-Gly-NH}_2 \tag{1a}$$

wherein Pro$^1$ and AA$^1$ are as described above for formula (1). Preferred tripeptides of formula (1a) include Pro-Trp-Gly-NH$_2$, Pro-Arg-Gly-NH$_2$, Pro-D-Arg-Gly-NH$_2$, Pro-Lys-Gly-NH$_2$, Pro-Orn-Gly-NH$_2$, and Pro-Ile-Gly-NH$_2$.

Another embodiment of tripeptides of formula (1) useful in treating physiological, psychosomatic, neurological or psychiatric disorders in patients includes compounds having formula (1b):

$$R^1\text{-Pro}^1\text{-AA}^1\text{-Gly-NH}_2 \quad (1b)$$

wherein Pro$^1$, AA$^1$ and R$^1$ are as described above for formula (1). Preferred compositions of the tripeptides of formula (1b) include cis- or trans-4-OH-Pro-D-Arg-Gly-NH$_2$, cis- or trans-4-OH-Pro-Ile-Gly-NH$_2$, cis- or trans-4-OH-Pro-Arg-Gly-NH$_2$, cis- or trans-4-OH-Pro-Trp-Gly-NH$_2$, and cis- or trans-4-thio-Pro-Leu-Gly-NH$_2$.

A further embodiment of tripeptides of formula (1) useful for treating physiological, psychosomatic, neurological or psychiatric disorders in patients is formula (1c):

$$\text{Pro}^1\text{-AA}^1\text{-NR}^2\text{—CH}_2\text{—R} \quad (1c)$$

wherein Pro$^1$, AA$^1$, R and R$^2$ are as described above for formula (1), with the proviso that where Pro$^1$ is Pro and AA$^1$ is Leu, R$^2$ is not a hydrogen atom when R is either a carboxyl group or a hydroxyalkyl group, and with the further proviso that where Pro$^1$ is Pro and AA$^1$ is Trp, R$^2$ is not a hydrogen atom when R is a hydroxyalkyl group. Preferred compositions of the tripeptides of formula (1c) include, but are not necessarily limited to Pro-Leu-N(CH$_3$)CH$_2$—CONH$_2$ (or Pro-Leu-Sar-NH$_2$) and Pro-Trp-NHCH$_2$—CO$_2$H (or Pro-Trp-Gly).

In yet a further embodiment, tripeptides useful for utilization in treating physiological, psychosomatic, neurological or psychiatric disorders in patients are represented by formula (2):

$$R^1\text{-Pro}^1\text{-AA}^1\text{-Ala-R} \quad (2)$$

where Pro$^1$ represents the amino acid Pro or dehydro-Pro, preferably 3,4-dehydro Pro; AA$^1$ represents an amino acid of the group of Arg or D-Arg; R represents a carboxyl group, a hydroxyalkyl group, a carbamyl group, an alkylcarbamyl group, or an alkoxycarbonyl; and, R$^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of the tripeptides of formula (2) disclosed for utilization in treating physiological, psychosomatic, neurological or psychiatric disorders in patients is represented by formula (2a):

$$\text{Pro}^1\text{-AA}^1\text{-Ala-NH}_2 \quad (2a)$$

wherein Pro$^1$ and AA$^1$ are as described above for formula (2). Preferred compositions of the tripeptides of formula (2a) include Pro-Arg-Ala-NH$_2$ and Pro-D-Arg-Ala-NH$_2$.

In yet another embodiment, tripeptides of the present invention useful in treating physiological, psychosomatic, neurological or psychiatric disorders in patients are represented by formula (3):

$$R^1\text{-Pro}^1\text{-AA}^1\text{-Tyr-R} \quad (3)$$

where Pro$^1$ represents the amino acid Pro or dehydro-Pro, preferably 3,4-dehydro Pro; AA$^1$ represents the amino acid Orn; R represents a carboxyl group, a hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or a dimethyl or diethylamino group.

An embodiment of the tripeptides of formula (3) disclosed for utilization in treating physiological, psychosomatic, neurological or psychiatric disorders in patients is formula (3a):

$$R^1\text{-Pro}^1\text{-AA}^1\text{-Tyr-NH}_2 \quad (3a)$$

where Pro$^1$, AA$^1$ and R$^1$ are as described for formula (3). Preferred compositions of the tripeptides of formula (3a) include Pro-Orn-Tyr-NH$_2$ and cis- or trans-4-OH-Pro-Orn-Tyr-NH$_2$.

The present invention also provides tetrapeptides and use thereof in treating physiological, psychosomatic, neurological or psychiatric disorders. One embodiment provides tetrapeptide compositions represented by formula (4):

$$R^1\text{-Pro}^1\text{-AA}^1\text{-Gly-AA}^2\text{-R} \quad (4)$$

where Pro$^1$ represents the amino acid Pro or dehydro-Pro, preferably 3,4-dehydro Pro; AA$^1$ represents Ile, Leu, Arg, D-Arg or Trp; AA$^2$ represents an amino acid of the group of Trp or Tyr; R represents a carboxyl group, hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of tetrapeptides of formula (4) useful for treating physiological, psychosomatic, neurological or psychiatric disorders in patients is formula (4a):

$$R^1\text{-Pro}^1\text{-AA}^1\text{-Gly-AA}^2\text{-NH}_2 \quad (4a)$$

wherein Pro$^1$, AA$^1$, AA$^2$, and R$^1$ are as described for formula (4). Preferred compositions of the tetrapeptides of formula (4a) include cis- or trans-4-OH-Pro-Leu-Gly-Trp-NH$_2$ (SEQ ID NO:1), cis- or trans-4-OH-Pro-Ile-Gly-Trp-NH$_2$ (SEQ ID NO:2), cis- or trans-4-OH-Pro-D-Arg-Gly-Trp-NH$_2$, 3,4-dehydro-Pro-D-Arg-Gly-Trp-NH$_2$ and 3,4-dehydro-Pro-Arg-Gly-Trp-NH2 (SEQ ID NO:62).

A further embodiment of tetrapeptides of formula (4) disclosed for utilization in treating physiological, psychosomatic, neurological or psychiatric disorders in patients is formula (4b):

$$\text{Pro}^1\text{-AA}^1\text{-Gly-AA}^2\text{-NH}_2 \quad (4b)$$

wherein Pro$^1$, AA$^1$ and AA$^2$ are as described for formula (4). Preferred compositions of the tetrapeptides of formula (4b) include Pro-Ile-Gly-Trp-NH$_2$ (SEQ ID NO:3), 3,4-dehydro-Pro-Ile-Gly-Trp-NH$_2$ (SEQ ID NO:4), Pro-Leu-Gly-Trp-NH$_2$ (SEQ ID NO:5), Pro-Leu-Gly-Tyr-NH$_2$ (SEQ ID NO:6), Pro-Arg-Gly-Trp-NH$_2$ (SEQ ID NO:7), Pro-Trp-Gly-Trp-NH$_2$ (SEQ ID NO:8), Pro-D-Arg-Gly-Trp-NH$_2$, and Pro-Ile-Gly-Tyr-NH$_2$ (SEQ ID NO:9).

Another embodiment provides N-terminus end enhanced tetrapeptide compositions represented by formula (5):

$$R^1\text{-AA}^1\text{-R}^2\text{-Pro}^1\text{-AA}^2\text{-Gly-R} \quad (5)$$

where Pro$^1$ represents the amino acid Pro or dehydro-Pro, preferably 3,4-dehydro Pro; AA$^1$ represents an amino acid selected from Trp, Tyr and Phe; AA$^2$ represents an amino acid selected from Leu, Ile, and Trp; R represents a carboxyl group, hydroxyalkyl group, a carbamyl group, an alkylcarbamyl group, or an alkoxycarbonyl group; and, $R^1$ and $R^2$ each independently represent a hydrogen atom; a lower alkyl group, preferably having 1 to 3 carbon atoms; a halogen atom, preferably a fluorine or chlorine atom; a hydroxyl group; a sulphydryl group; or an alkylamino or dialkylamino group, preferably a methyl or ethylamino or dimethyl or diethylamino group.

One embodiment of tetrapeptides of formula (5) useful in treating, physiological, psychosomatic, neurological or psychiatric disorders in patients is represented by formula (5a):

$$R^1\text{-}AA^1\text{-}R^2\text{-}Pro^1\text{-}AA^2\text{-}Gly\text{-}NH_2 \qquad (5a)$$

wherein $Pro^1$, $AA^1$, $AA^2$, $R^1$ and $R^2$ are as described for formula (5), with the proviso that where $Pro^1$ is Pro, $R^1$ and $R^2$ are not both hydrogen atoms when $AA^1$ is Tyr and $AA^2$ is Trp; and with the further proviso that when $Pro^1$ is Pro, and $AA^2$ is Leu, and $AA^1$ is Phe or Tyr, then $R^1$ and $R^2$ are not both hydrogen atoms. Preferred compositions of the tetrapeptides of formula (5a) include Trp-Pro-Leu-Gly-NH$_2$ (SEQ ID NO:10), Phe-Pro-Leu-Gly-NH$_2$ (SEQ ID NO:11), 4-F-Phe-Pro-Leu-Gly-NH$_2$ (SEQ ID NO:12), 4-Cl-Phe-Pro-Leu-Gly-NH$_2$ (SEQ ID NO:13), 4-F-Phe-Pro-Ile-Gly-NH$_2$ (SEQ ID NO:14), 4-F-Phe-cis- or trans-4-OH-Pro-Leu-Gly-NH$_2$ (SEQ ID NO:15), 4-F-Phe-cis- or trans-4-OH-Pro-Ile-Gly-NH$_2$ (SEQ ID NO:16), Trp-Pro-Leu-Gly-NH$_2$ (SEQ ID NO:17), Trp-Pro-Ile-Gly-NH$_2$ (SEQ ID NO:18), Trp-cis- or trans-4-OH-Pro-Leu-Gly-NH$_2$ (SEQ ID NO:19), Trp-cis- or trans-4-OH-Pro-Ile-Gly-NH$_2$ (SEQ ID NO:20), and 4-Cl-Phe-cis- or trans-4-OH-Pro-Ile-Gly-NH$_2$ (SEQ ID NO:60).

Another embodiment of tetrapeptides of formula (5) useful in treating physiological, psychosomatic, neurological or psychiatric disorders in patients is formula (5b):

$$R^1\text{-}AA^1\text{-}R^2\text{-}Pro^1\text{-}AA^2\text{-}Gly\text{-}R \qquad (5b)$$

wherein $Pro^1$, $AA^1$, $AA^2$, $R^1$, $R^2$ and R are as described for formula (5). Preferred compositions of the tetrapeptides of formula (5b) include compounds wherein the N-terminus heterocyclic nitrogen ring of $Pro^1$ is replaced by a cis- or trans-4-OH— group. In some preferred embodiments of compositions represented by formula (5b), $AA^2$ is Arg. A preferred peptide of formula (5b) is 4-F-Phe-cis- or trans-4-OH-Pro-Arg-Gly-1,2,3,4-Tetrahydroisoquinoline-3-carboxamide (SEQ NO:75).

The present invention further provides pentapeptides and use thereof in treating physiological, psychosomatic, neurological or psychiatric disorders. One embodiment of the pentapeptides provides N-terminus enhanced pentapeptide compositions represented by formula (6):

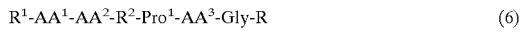

$$R^1\text{-}AA^1\text{-}AA^2\text{-}R^2\text{-}Pro^1\text{-}AA^3\text{-}Gly\text{-}R \qquad (6)$$

where $Pro^1$ represents the amino acid Pro or dehydro-Pro, preferably 3,4-dehydro Pro; $AA^1$ and $AA^2$ each independently represent an amino acid of the group of Phe or Tyr; $AA^3$ represents an amino acid of the group of Leu or Ile; R represents a carboxyl group, hydroxyalkyl group, a carbamyl group, an alkylcarbamyl group, or an alkoxycarbonyl group; and, $R^1$ and $R^2$ each independently represent a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of the pentapeptides of formula (6) useful in treating physiological, psychosomatic, neurological or psychiatric disorders in patients is formula (6a):

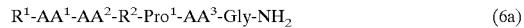

$$R^1\text{-}AA^1\text{-}AA^2\text{-}R^2\text{-}Pro^1\text{-}AA^3\text{-}Gly\text{-}NH_2 \qquad (6a)$$

wherein $Pro^1$, $AA^1$, $AA^2$, $R^1$, and $R^2$ are as described for formula (6). Preferred compositions of the pentapeptides of formula (6a) include 4-F-Phe-Tyr-Pro-Leu-Gly-NH$_2$ (SEQ ID NO:21), 4-Cl-Phe-Tyr-Pro-Leu-Gly-NH$_2$ (SEQ ID NO:22), Phe-Tyr-Pro-Leu-Gly-NH$_2$ (SEQ ID NO:23), Phe-Tyr-Pro-Ile-Gly-NH$_2$ (SEQ ID NO:24), Phe-Tyr-cis- or trans-4-OH-Pro-Leu-Gly-NH$_2$ (SEQ ID NO:25); Phe-Tyr-cis- or trans-4-OH-Pro-Ile-Gly-NH$_2$ (SEQ ID NO:26), Tyr-Tyr-Pro-Leu-Gly-NH$_2$ (SEQ ID NO:27), Tyr-Tyr-Pro-Ile-Gly-NH$_2$ (SEQ ID NO:28), Tyr-Tyr-cis- or trans-4-OH-Pro-Leu-Gly-NH$_2$ (SEQ ID NO:29), and Tyr-Tyr-cis- or trans-4-OH-Pro-Ile-Gly-NH$_2$ (SEQ ID NO:30).

Another embodiment of the pentapeptides provides combined N-terminus- and C-terminus-enhanced pentapeptide compositions represented by formula (7):

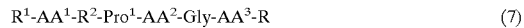

$$R^1\text{-}AA^1\text{-}R^2\text{-}Pro^1\text{-}AA^2\text{-}Gly\text{-}AA^3\text{-}R \qquad (7)$$

where $Pro^1$ represents the amino acid Pro or dehydro-Pro, preferably 3,4-dehydro Pro; $AA^1$ represents an amino acid of the group of Phe or Tyr; $AA^2$ represents an amino acid of the group of Leu, Ile, Arg, D-Arg, or Trp; $AA^3$ represents the amino acid Trp; R represents a carboxyl group, hydroxyalkyl group, a carbamyl group, an alkylcarbamyl group, or an alkoxycarbonyl group; and, $R^1$ and $R^2$ each independently represent a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of pentapeptides of formula (7) useful in treating physiological, psychosomatic, neurological or psychiatric disorders in patients is represented by formula (7a):

$$R^1\text{-}AA^1\text{-}R^2\text{-}Pro^1\text{-}AA^2\text{-}Gly\text{-}Trp\text{-}NH_2 \qquad (7a)$$

wherein $Pro^1$, $AA^1$, $AA^2$, $R^1$ and $R^2$ are as described for formula (7). Preferred compositions of the pentapeptides of formula (7a) include Phe-Pro-Leu-Gly-Trp-NH$_2$ (SEQ ID NO:31), Tyr-Pro-Leu-Gly-Trp-NH$_2$ (SEQ ID NO:32), Phe-cis- or trans-4-OH-Pro-Leu-Gly-Trp-NH$_2$ (SEQ ID NO:33), Phe-Pro-Ile-Gly-Trp-NH$_2$ (SEQ ID NO:34), Phe-cis- or trans-4-OH-Pro-Ile-Gly-Trp-NH$_2$ (SEQ ID NO:35), Tyr-cis- or trans-4-OH-Pro-Leu-Gly-Trp-NH$_2$ (SEQ ID NO:36), Tyr-Pro-Ile-Gly-Trp-NH$_2$ (SEQ ID NO:37), Tyr-cis- or trans-4-OH-Pro-Leu-Gly-Trp-NH$_2$ (SEQ ID NO:38), Tyr-Pro-Trp-Gly-Trp-NH$_2$ (SEQ ID NO:39), Tyr-cis- or trans-4-OH-Pro-Trp-Gly-Trp-NH$_2$ (SEQ ID NO:40), 4-F-Phe-cis- or trans-4-OH-Pro-Ile-Gly-Trp-NH$_2$ (SEQ ID NO:41), 4-F-Phe-cis- or trans-4-OH-Pro-Leu-Gly-Trp-NH$_2$ (SEQ ID NO:42), 4-F-Phe-cis- or trans-4-OH-Pro-Arg-Gly-Trp-NH$_2$ (SEQ ID NO:43), 4-F-Phe-cis- or trans-4-OH-Pro-D-Arg-Gly-Trp-NH$_2$, 3-F-Phe-cis- or trans-4-OH-Pro-Arg-Gly-Trp-NH$_2$ (SEQ ID NO:66); 2-F-Phe-cis- or trans-4-OH-Pro-Arg-Gly-Trp-NH$_2$ (SEQ ID NO:68); and 4-Cl-Phe-cis- or trans-4-OH-Pro-Arg-Gly-Trp-NH$_2$ (SEQ ID NO:61).

Additional preferred compositions of the pentapeptides of formula (7a) are characterized by the optional modification of $Pro^1$ to dehydro-Pro, preferably 3,4-dehydro-Pro. Additional preferred peptides of formula (7a) include 4-F-Phe-3,4-dehydro-Pro-Ile-Gly-Trp-NH$_2$ (SEQ ID NO:72) and 4-F-Phe-3,4-dehydro-Pro-Arg-Gly-Trp-NH$_2$ (SEQ ID NO:55).

Additional preferred pentapeptides of formula (7a) include pentapeptides having modifications at AA², preferably Arg, His, Homo-Arg, L-Allo-Ile or canavanine; additional optional modifications at R¹ and/or R² (preferably R¹) and preferably an amino group, a carboxyl group, a nitro group, or a phosphono group (preferably as phosphono-Try); additional optional modification of the heterocyclic nitrogen ring of Pro¹, preferably cis- or trans-4-OH or Homo-Pro. Exemplary additional preferred peptides of formula (7a) are 4-NH₂-Phe-cis- or trans-4-OH-Pro-Arg-Gly-Trp-NH₂ (SEQ ID NO: 63); 4-F-Phe-cis- or trans-4-OH-Pro-His-Gly-Trp-NH₂ (SEQ ID NO: 64); 4-NO₂-Phe-cis- or trans-4-OH-Pro-Arg-Gly-Trp-NH₂ (SEQ ID NO: 65); 4-CH₃O-Phe-cis- or trans-4-OH-Pro-Arg-Gly-Trp-NH₂ (SEQ ID NO:59); 4-F-Phe-cis- or trans-4-OH-Pro-Homo-Arg-Gly-Trp-NH₂ (SEQ ID NO:71); 4-F-Phe-Homo-Pro-Ile-Gly-Trp-NH₂ (SEQ ID NO: 69); 4-F-Phe-Homo-Pro-Arg-Gly-Trp-NH₂ (SEQ ID NO:57); and 4-F-Phe-cis- or trans-4-OH-Pro-L-Allo-Ile-Gly-Trp-NH₂ (SEQ ID NO:73).

Another embodiment of pentapeptides of formula (7) useful in treating physiological, psychosomatic, neurological or psychiatric disorders in patients is compounds having formula (7b):

$$R^1\text{-}AA^1\text{-}R^2\text{-}Pro^1\text{-}AA^2\text{-}Gly\text{-}Trp\text{-}NH_2 \quad (7b)$$

wherein AA¹ is Phe; and Pro¹, AA², R¹ and R² are as described for formula (7), with the optional modification of the N-terminus heterocyclic nitrogen ring of Pro¹ with a substituent selected from the group consisting of cis-4-OH—, trans-4-OH—, cis-3-OH— and trans-3-OH. In some embodiments, the pentapeptides may be further modified at R¹, preferably by two or more halogen atoms, or a cyano group. Preferred compositions of the pentapeptides of formula (7b) include 3,4-Dichloro-Phe-cis- or trans-4-OH-Pro-Arg-Gly-Trp-NH₂ (SEQ NO:76), 4-NC-Phe-cis- or trans-4-OH-Pro-Arg-Gly-Trp-NH₂ (SEQ NO:77), 4-F-Phe-cis- or trans-4-OH-Pro-D-Leu-Gly-Trp-NH₂ (SEQ NO:78), 4-F-Phe-trans-3-Hydroxy-Pro-Arg-Gly-Trp-NH₂ (SEQ NO:79).

Another embodiment of pentapeptides of formula (7) useful in treating physiological, psychosomatic, neurological or psychiatric disorders in patients is formula (7c):

$$R^1\text{-}AA^1\text{-}R^2\text{-}Pro^1\text{-}AA^2\text{-}Gly\text{-}Trp \quad (7c)$$

wherein Pro¹, AA¹, AA², R¹ and R² are as described for formula (7) with additional optional modifications at AA², preferably Homo-Arg; and additional optional modification of the N-terminus heterocyclic nitrogen ring of Pro¹ with a substituent selected from the group consisting of cis-4-OH—, trans-4-OH—, cis-4-OH— and trans-3-OH—. A preferred composition of the pentapeptides of formula (7c) is 4-F-Phe-cis- or trans-4-OH-Pro-Homo-Arg-Gly-Trp (SEQ ID NO:74).

Another embodiment of pentapeptides of formula (7) useful in treating physiological, psychosomatic, neurological or psychiatric disorders in patients is formula (7d):

$$R^1\text{-}AA^1\text{-}R^2\text{-}Pro^1\text{-}AA^2\text{-}Gly\text{-}AA^3\text{-}R \quad (7d)$$

wherein Pro¹, AA¹, AA², AA³, R¹, R² and R are as described for formula (7). In some embodiments, the N-terminus heterocyclic nitrogen ring of Pro¹ has a substituent selected from the group consisting of cis-4-OH—, trans-4-OH—, cis-3-OH—, and trans-3-OH—. In some embodiments the pentapeptide is modified at, Pro¹, preferably Homo-Pro. In some embodiments, the pentapeptide is modified at AA¹, preferably PhenylGly. In some embodiments, the pentapeptide is modified at AA³, preferably. In some embodiments, the pentapeptide is modified at R¹, preferably a haloform or a methoxyl group. In some embodiments, the pentapeptide is modified at R, preferably two or more halogen atoms or a hydroxyamino group.

Preferred compositions of the pentapeptides of formula (7d) include 4-CH₃O-Phe-3,4-Dehydro-Pro-Arg-Gly-Trp-NH₂ (SEQ NO:81), 2,4-Di-F-Phe-3,4-Dihydro-Pro-Arg-Gly-Trp-NH₂ (SEQ NO:82), 4-CF₃-Phe-3,4-Dehydro-Pro-Arg-Gly-Trp-NH₂ (SEQ NO:83), 4-F-PhenylGly-3,4-Dehydro-Pro-Arg-Gly-Trp-NH₂ (SEQ NO:84), 3-F-Tyr-3,4-Dehydro-Pro-Arg-Gly-Trp-NH₂ (SEQ NO:85), 4-F-Phe-3,4-Dehydro-Pro-Arg-Gly-Trp-NHOH (SEQ NO:86), 3,4-Di-Cl-Phe-3,4-Dihydro-Pro-Arg-Gly-Trp-NH₂ (SEQ NO:87), 2-F-Tyr-3,4-Dehydro-Pro-Arg-Gly-Trp-NH₂ (SEQ NO:88), 4-F-Phe-3,4-Dehydro-Pro-Arg-Gly-7-AzaTrp-NH₂ (SEQ NO:89).

Another embodiment of pentapeptides of formula (7) useful in treating physiological, psychosomatic, neurological or psychiatric disorders in patients is formula (7e):

$$R^1\text{-}AA^1\text{-}R^2\text{-}Pro^1\text{-}AA^2\text{-}Gly\text{-}R^4\text{-}Trp\text{-}NH_2 \quad (7e)$$

wherein Pro¹, AA¹, AA², R¹ and R² are as described for formula (7). Optionally, the N-terminus heterocyclic nitrogen ring of Pro¹ may be modified with a substituent selected from the group consisting of cis-4-OH—, trans-4-OH—, cis-3-OH—, and trans-3-OH—. R⁴ represents a modification of the tryptophan residue at one of C4, C5, C6 and C7 with a halogen atom, a hydroxyl group, or an alkyl group. Preferred compositions of the pentapeptides of formula (7e) include 4-F-Phe-cis- or trans-4-OH-Pro-Arg-Gly-4-F-Trp-NH₂ (SEQ NO:107), 4-F-Phe-cis- or trans-4-OH-Pro-Arg-Gly-7-Methyl-Trp-NH₂ (SEQ NO:108).

Another embodiment of pentapeptides of formula (7) useful in treating physiological, psychosomatic, neurological or psychiatric disorders in patients is formula (7f):

$$R^1\text{-}AA^1\text{-}R^2\text{-}Pro^1\text{-}R^5\text{-}AA^2\text{-}Gly\text{-}Trp\text{-}NH_2 \quad (7f)$$

wherein Pro¹, AA¹, AA², R¹ and R² are as described for formula (7). In some embodiments the N-terminus heterocyclic nitrogen ring of Pro¹ is modified with a substituent selected from the group consisting of cis-4-OH—, trans-4-OH—, cis-3-OH—, and trans-3-OH—. R⁵ represents at least one halogen atom. A preferred composition of the pentapeptides of formula (7f) is 4-F-Phe-cis- or trans-4-OH-Pro-5,5,5-Trifluoro-Leu-Gly-Trp-NH₂ (SEQ NO:109).

Another embodiment of pentapeptides of formula (7) useful in treating physiological, psychosomatic, neurological or psychiatric disorders in patients is formula (7g):

$$R^1\text{-}AA^1\text{-}R^2\text{-}Pro^1\text{-}AA^2\text{-}Gly\text{-}R^4\text{-}AA^3\text{-}R \quad (7g)$$

wherein Pro¹, AA¹, AA², AA³, R¹, R² and R are as described for formula (7). In some embodiments, Pro¹ is modified preferably Homo-Pro. In some embodiments, the N-terminus heterocyclic nitrogen ring of Pro¹ is modified with a substituent selected from the group consisting of cis-4-OH—, trans-4-OH—, cis-3-OH—, and trans-3-OH—. R⁴ represents a halogen atom, a methyl group, a methoxyl group or a hydroxyl group. Preferred compositions of the pentapeptides of formula (7g) include 4-F-Phe-3,4-Dehydro-Pro-Arg-Gly-4-F-Trp-NH₂ (SEQ NO:90), 4-F-Phe-3,4-Dehydro-Pro-Arg-Gly-5-F-Trp-NH₂ (SEQ NO:91), 4-F-Phe-3,4-Dihydro-Pro-Arg-Gly-6-F-Trp-NH₂ (SEQ NO:92), 4-F-Phe-3,4-Dehydro-Pro-Arg-Gly-3-CH₃O-Trp-NH₂ (SEQ NO:93), 4-F-Phe-3,4-Dehydro-Pro-Arg-Gly-N-Methyl-Trp-NH₂ (SEQ NO:94), 4-F-Phe-3,4-Dehydro-Pro-Arg-Gly-1-Methyl-Trp-NH₂ (SEQ NO:95), 4-F-Phe-3,4-

Dehydro-Pro-Arg-Gly-4-Methyl-Trp-NH$_2$ (SEQ NO:96), 4-F-Phe-3,4-Dehydro-Pro-Arg-Gly-5-Methyl-Trp-NH$_2$ (SEQ NO:97), 4-F-Phe-3,4-Dehydro-Pro-Arg-Gly-6-Methyl-Trp-NH$_2$ (SEQ NO:98), 4-F-Phe-3,4-Dehydro-Pro-Arg-Gly-5-Hydroxy-Trp-NH$_2$ (SEQ NO:99).

Another embodiment provides internal and C-terminus enhanced pentapeptide compositions represented by formula (8):

$$R^1\text{-}Pro^1\text{-}AA^1\text{-}AA^2\text{-}Gly\text{-}AA^3\text{-}R \qquad (8)$$

where Pro$^1$ represents the amino acid Pro or dehydro-Pro, preferably 3,4-dehydro Pro; AA$^1$ and AA$^2$ each independently represent an amino acid of the group of Leu or Ile; AA$^3$ represents the amino acid Trp; R represents a carboxyl group, a hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino group or dimethyl or diethylamino group.

An embodiment of pentapeptides of formula (8) useful in treating physiological, psychosomatic, neurological or psychiatric disorders in patients is represented by formula (8a):

$$R^1\text{-}Pro^1\text{-}AA^1\text{-}AA^2\text{-}Gly\text{-}Trp\text{-}NH_2 \qquad (8a)$$

wherein Pro$^1$, AA$^1$, AA$^2$, and R$^1$ are as described for formula (8). Preferred compositions of the pentapeptides of formula (8a) include Pro-Ile-Leu-Gly-Trp-NH$_2$ (SEQ ID NO:44) and cis- or trans-4-OH-Pro-Ile-Leu-Gly-Trp-NH$_2$ (SEQ ID NO: 45).

In another embodiment of the invention, pentapeptide compositions or pharmaceutically acceptable salts thereof including addition of both a N-terminus amino acid and a C-terminus amino acid can be represented by the following formula (9):

$$R^1\text{-}AA^1\text{-}R^2\text{-}Pro^1\text{-}AA^2\text{-}Gly\text{-}AA^3\text{-}R \qquad (9)$$

where Pro$^1$ represents the amino acid Pro or dehydro-Pro, preferably 3,4-dehydro Pro; AA$^1$ represents the amino acid Ala; AA$^2$ represents an amino acid of the group of Leu, Ile, Arg, D-Arg, Trp, or canavanine; AA$^3$ represents the amino acid Trp; R represents a carboxyl group, hydroxyalkyl group, a carbamyl group, an alkylcarbamyl group, or an alkoxycarbonyl group; and, R$^1$ represents a pyridyl ring, preferably as a 3-(3-pyridyl) moiety; R$^2$ represents a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or dimethyl or diethylamino group.

A preferred composition of formula (9) is 3-(3-pyridyl)-Ala-cis- or trans-4-OH-Pro-Arg-Gly-Trp-NH$_2$ (SEQ ID NO:70).

In another embodiment of the invention, hexapeptide compositions or pharmaceutically acceptable salts thereof including addition of both a N-terminus amino acid and a C-terminus amino acid can be represented by the following formula (10):

$$R^1\text{-}AA^1\text{-}R^2\text{-}Pro^1\text{-}AA^2\text{-}AA^4\text{-}Gly\text{-}AA^3\text{-}R \qquad (10)$$

where Pro$^1$ represents the amino acid Pro or dehydro-Pro; AA$^1$ represents an amino acid of the group of Phe or Tyr; AA$^2$ represents an amino acid of the group of Leu, Ile, Arg, D-Arg, Trp, or canavanine; AA$^3$ represents the amino acid Trp; AA$^4$ represents the amino acid Gly or Ile; R represents a carboxyl group, hydroxyalkyl group, a carbamyl group, an alkylcarbamyl group, or an alkoxycarbonyl group; and, R$^1$ and R$^2$ each independently represent a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or dimethyl or diethylamino group.

A preferred composition of formula (10) is 4-F-Phe-3,4-Dehydro-Pro-Arg-Gly-Gly-Trp-NH$_2$ (SEQ NO:80).

A group of preferred compositions of the hexapeptides of formula (10) which may be utilized alone or in combination with other peptides disclosed herein to treat patients suffering from physiological, psychosomatic, neurological or psychiatric disorders includes hexapeptides characterized by addition of a C-terminus amino acid of Trp, optional modification of the heterocyclic nitrogen ring of Pro$^1$, preferably a cis- or trans-4-OH group, a fluorine atom at position 4 of Phe. Preferably, the hexapeptides include Arg at AA$^2$; Trp at AA$^3$; and Ile or Gly at AA$^4$, and the C-terminus amide remains unmodified. Exemplary hexapeptides are represented by formula (10a):

$$R^1\text{-}Phe\text{-}R^2\text{-}Pro^1\text{-}AA^2\text{-}AA^4\text{-}Gly\text{-}Trp\text{-}NH_2 \qquad (10a)$$

wherein R$^1$, R$^2$, AA$^2$, and AA$^4$ are as defined above for formula (1). Preferred peptides of formula (10a) include 4-F-Phe-cis- or trans-4-OH-Pro-Arg-Gly-Gly-Trp-NH$_2$ (SEQ ID NO:58) and 4-F-Phe-cis- or trans-4-OH-Pro-Arg-Ile-Gly-Trp-NH$_2$ (SEQ ID NO:67).

Another embodiment of the invention provides heptapeptide compositions or pharmaceutically acceptable salts thereof, including addition of both a N-terminus amino acid and a C-terminus amino acid can be represented by the following formula (11):

$$R^1\text{-}AA^1\text{-}R^2\text{-}Pro^1\text{-}AA^2\text{-}AA^4\text{-}AA^5\text{-}Gly\text{-}AA^3\text{-}R \qquad (11)$$

where Pro$^1$ represents the amino acid Pro or dehydro-Pro; AA$^1$ represents an amino acid of the group of Phe or Tyr; AA$^2$ represents an amino acid of the group of Leu, Ile, Arg, D-Arg, Trp, or canavanine; AA$^3$ represents the amino acid Trp; AA$^4$ and AA$^5$ represent the amino acid Gly or Ile; R represents a carboxyl group, hydroxyalkyl group, a carbamyl group, an alkylcarbamyl group, or an alkoxycarbonyl group; and, R$^1$ and R$^2$ each independently represent a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or dimethyl or diethylamino group, or a phosphono group (preferably as phosphono-tyrosine).

A preferred embodiment of a composition having formula (11) is 4-F-Phe-cis- or trans-4-OH-Pro-Arg-Gly-Ile-Gly-Trp-NH$_2$ (SEQ ID NO:56).

In another embodiment of the invention, tetrapeptide compositions or pharmaceutically acceptable salts thereof including the addition of an N-terminus amino acid of Phe to Arg; addition of a C-terminus amino acid of Trp to Gly; and modification of the aromatic ring of Phe can be represented by the following formula (12):

    (12)

R$^1$-Phe-R$^2$-Arg-Gly-Trp-NH$_2$ where R$^1$ represents a halogen atom and R$^2$ represents a carboxylic acid of a monocyclic organic compound with a three to six membered ring structure having a hetero nitrogen atom. Preferred compositions of the pentapeptides of formula (12) include, but are not necessarily limited to, 4-F-Phe-isonipecotic acid-Arg-Gly-Trp-NH$_2$(4-pyridinecarboxylic acid) (SEQ NO:100), 4-F-Phe-2-Carboxy-Azetidine-Arg-Gly-Trp-NH$_2$ (SEQ NO:101), 4-F-Phe-2-carboxy-Aziridine-Arg-Gly-Trp-NH$_2$ (SEQ NO:103), 4-F-Phe-3-Carboxy-1,4,5,6-Tetrahydropyridine-Arg-Gly-Trp-NH$_2$ (SEQ NO:105), 4-F-Phe-2-Carboxypyrrole-Arg-Gly-Trp-NH$_2$ (SEQ NO:106).

In another embodiment of the invention, pentapeptide compositions or pharmaceutically acceptable salts thereof including replacement of Pro with Arg; addition of an N-terminus amino acid of Phe to Arg; addition of an internal amino acid; addition of a C-terminus amino acid of Trp to Gly; and modification of the aromatic ring of Phe can be represented by the following formula (13):

    (13)

R$^1$-Phe-AA$^1$-Arg-Gly-Trp-NH$_2$ where AA$^1$ represents an amino acid selected from the group comprising 1-amino-1-carboxycyclopentane and 1-amino-1-carboxy-cyclopropyl and R$^1$ represents a halogen atom. Preferred compositions of the pentapeptides of formula (13) include 4-F-Phe-1-Amino-1-Carboxycyclopentane-Arg-Gly-Trp-NH$_2$ (SEQ NO:102) and 4-F-Phe-1-Amino-1-Carboxy-Cyclopropyl-Arg-Gly-Trp-NH$_2$ (SEQ NO:104).

In some embodiments, in peptide compositions represented by any of formula (7), (8), (9), (10), or (11), Gly may be replaced by Val, Sar or Ala. One preferred peptide composition wherein Gly is substituted with Sar in formula (7) is 4-F-Phe-3,4-Dehydro-Pro-Arg-Sar-Trp-NH$_2$ (SEQ NO:110).

Preferred compositions of the present invention are peptides that show higher activity in the Porsolt swim test than known compounds for treating depression and/or anxiety, including SSRIs and MIF. The preferred peptides may vary in length, with particularly preferred peptides being tetrapeptides, pentapeptides, hexapeptides and heptapeptides. Exemplary particularly preferred peptides may be represented by the formula:

R$^1$-Phe-Pro$^1$-AA$^2$-AA$^3$-NH$_2$, for a tetrapeptide, wherein R$^1$ is preferably a halogen atom, most preferably a fluorine or chlorine atom, a carboxyl group, an amino group or a nitro group, with all modifications preferably at the C4 atom of Phe; Pro$^1$ is 3,4-dehydro Pro, Homo-Pro, cis- or trans-4OH-Pro or Pro, as listed in order of preference, AA$^2$ is preferably Ile, Leu or Arg; and AA$^3$ is preferably Gly or Trp.

A highly preferred tetrapeptide is Pro-Ile-Gly-Trp (SEQ ID NO: 3).

Preferred pentapeptides, hexapeptides and heptapeptides, according to the invention, are represented by the formula:

R$^1$-Phe-Pro$^1$-AA$^2$-Gly-AA$_{(n)}$-AA$^3$-NH$_2$, wherein R$^1$ is preferably a halogen atom, preferably a fluorine or chlorine atom, a carboxyl group, an amino group or a nitro group, with all modifications preferably at the C4 atom of Phe; Pro$^1$ is 3,4-dehydro Pro, Homo-Pro, cis- or trans-4OH-Pro or Pro, as listed in order of preference, AA$^2$ is preferably Arg, Ile, Leu or His, with Arg being especially preferred; AA$_{(n)}$ is 0–2 amino acid residues, if n=1, then Gly is preferred and if n=2, then Ile-Gly, Ile-Ile or Gly-Gly is preferred; AA$^3$ is preferably Trp or Gly, with Trp most preferred.

Also within the scope of the present invention are combinations of any of the peptides of formula (1) through formula (11) and the use of such combinations in treating physiological, psychosomatic, neurological or psychiatric disorders in patients. Also included are chemically combined polypeptides formed by combining two or more of the peptides disclosed herein. Such chemically combined polypeptides preferably comprise from at least about three to at least about ten modified and/or unmodified amino acids.

The present invention further provides admixtures of one or more of the peptides of formula (1) through formula (11) with known antidepressant compounds such as amitriptyline, fluoxetine (Prozac) and sertraline (Zoloft). It is within the ordinary skill of the artisan to generate various admixtures with the peptides of the present invention beyond the exemplifications disclosed throughout this specification.

The peptides of the present invention are preferably formulated in a suitable pharmaceutical carrier for in vivo administration to the patient by any standard method known in the art such that a pharmacologically effective concentration reaches the site of action. For the methods and compositions disclosed herein for treating physiological, psychosomatic, neurological, psychological or psychiatric disorders, the preferred site of action is the brain. Exemplary routes of administration include oral (mouth or peroral administration), sublingual, parenteral (e.g., intravenous, intraspinal, intrathecal, intraventricular, epidermal, intracisternal, intracutaneous or intradermal, subcutaneous, or intramuscular), epicutaneous, transdermal, intranasal, vaginal, and rectal, as well as by inhalation in the form of, for example, a polydisperse or microdisperse aerosol.

The tripeptide hormone fragment having the general formula Pro-Leu-Gly-NH$_2$, otherwise known as L-prolyl L-leucyl glycine, melanocyte stimulating inhibitory factor, melanotrophic release inhibiting factor, or MIF, is known to exhibit antidepressant activity. MIF is typically reported in literature as having the tripeptide structure Pro-Leu-Gly-NH$_2$ or Pro-Leu-Gly-amide. MIF is also referred to herein as Pro-Leu-Gly-NH$_2$.

It has been found that modifications of the tripeptide structure of MIF result in novel peptides useful in treating patients suffering from physiological, psychosomatic, neurological, physiological or psychiatric disorders, including PMS, chronic fatigue syndrome, fibromyalgia and seasonal affective disorder. Such modifications target amino terminus residues, carboxyl terminus residues and internal residues, including addition and substitution of amino acid residues and modification of the peptide bonds and functional side groups of respective amino acid residues as more fully described hereinbelow. Peptides produced using such modifications, and the use of such peptides in treating physiological, psychosomatic, neurological, physiological or psychiatric disorders, are within the scope of the present invention, and may be administered according to the routes disclosed herein.

In general, peptides within the scope of the present invention can be made using known amino acids, such as for example, Ala, Arg, D-Arg, Gly, Ile, Leu, D-Leu, Lys, Orn, Phe, Pro, dehydro-Pro, Sar, Trp, and Tyr. Preferred peptides are made by additions or substitutions at the amino terminus (N-terminus), carboxyl terminus (C-terminus) and/or additions or substitutions of internal amino acid residues to the sequence Pro-Leu-Gly-NH$_2$. Carboxyl terminus modifications of the peptides of the invention can include replacement of the carbamyl (amide) group at the carboxyl terminus of Pro-Leu-Gly-NH$_2$ by, for example, a carboxyl (acid) group, a hydroxyalkyl (alcohol) group, an alkoxycarbonyl (ester) group, or an alkylcarbamyl (alkylated amide) group. Amino terminus and internal modifications of the peptides of the invention can include additions or eliminations on the heterocyclic, aromatic, and other carbon residues of the amino acids with an alkyl group, preferably an alkyl group having 1 to 3 carbon atoms, a dehydro (anhydro) group, a halo group, a hydroxyl group, a sulphydryl group, an alkylamino group, or a dialkylamino group. In some embodiments, the amino groups of the peptides of the invention can be alkylated, preferably with an alkyl group having 1 to 3 carbon atoms. Such additions, substitutions, eliminations, and/or modifications can be carried out by conventional polypeptide synthesis and organic chemistry synthesis techniques known to those skilled in the art.

The groupings of the peptides of the invention into the formulas described herein are provided only as a matter of convenience and should not be considered limiting in any manner.

In one embodiment, the peptides are tripeptides characterized either by optional replacement of the Leu residue of Pro-Leu-Gly-NH$_2$ with an amino acid selected from the group of Trp, Orn, Lys, Arg, D-Arg, or Ile; optional replacement of the Pro residue with dehydro-Pro, preferably 3,4-dehydro-Pro; optional modification of the carboxyl terminus amide group with a substituent selected from a carboxyl group, an hydroxyalkyl group, preferably a hydroxymethyl group, an alkoxycarbonyl group, or an alkylated carbamyl group; optional modification of the amino terminus heterocyclic group or dehydro-heterocyclic group with a substituent selected from the group of a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group; or an alkylamino group or a dialkylamino group, preferably a methyl or ethylamino or a dimethyl or diethylamino group; and/or optional modification of the hydrogen atoms at the nitrogen atoms of the amino acid peptide bonds with a lower alkyl group, preferably having 1 to 3 carbon atoms.

Tripeptides or pharmaceutically acceptable salts thereof can be represented by formula (1):

$$R^1\text{-Pro}^1\text{-AA}^1\text{-NR}^2\text{-CH}_2\text{-R} \tag{1}$$

where Pro$^1$ represents the amino acid Pro or dehydro-Pro, preferably 3,4-dehydro Pro; AA$^1$ represents an amino acid of the group of Trp, Orn, Lys, Leu, Arg, D-Arg, or Ile; R represents a carboxyl group, a hydroxyalkyl group, a carbamyl group, an alkylcarbamyl group, or an alkoxycarbonyl group; R$^1$ represents a hydrogen atom, a lower alkyl group, preferably having 1 to 3 carbon atoms, a halogen atom, preferably a fluorine or chlorine atom, a hydroxyl group, sulphydryl group, or an alkylamino or dialkylamino group, preferably a methyl or ethylamino group or dimethyl or diethylamino group; and, R$^2$ represents a hydrogen atom or a lower alkyl group, preferably having 1 to 3 carbon atoms, with the proviso that where Pro$^1$ is Pro and AA$^1$ is Leu, then R$^1$ and R$^2$ are not both hydrogen when R is a carbamyl (amide) group.

Some preferred tripeptides of formula (1) which may be utilized alone or in combination with other peptides disclosed herein to treat patients suffering from physiological, psychosomatic, neurological or psychiatric disorders are characterized by replacement of Leu, and are further characterized by having the N-terminus Pro$^1$ residue and C-terminus amide group remain unmodified, which can be represented by formula (1a). Formula (1a) is depicted as:

$$\text{Pro}^1\text{-AA}^1\text{-Gly-NH}_2 \tag{1a}$$

wherein Pro$^1$ and AA$^1$ are as described above for formula (1). The tripeptides of formula (1a), may be utilized alone or in combination with other peptides disclosed herein to treat patients suffering from physiological, psychosomatic, neurological or psychiatric disorders. Preferred compositions of the tripeptides of formula (1a) are:

Pro-Trp-Gly-NH$_2$;

Pro-Arg-Gly-NH$_2$;

Pro-D-Arg-Gly-NH$_2$;

Pro-Lys-Gly-NH$_2$;

Pro-Orn-Gly-NH$_2$;

and,

Pro-Ile-Gly-NH$_2$.

A second group of preferred compositions of the tripeptides of formula (1) which may be utilized alone or in combination with other peptides disclosed herein to treat patients suffering from physiological, psychosomatic, neurological or psychiatric disorders are characterized by optional replacement of Leu, and are further characterized by optional modification of the N-terminus heterocyclic nitrogen ring of Pro$^1$, preferably at the C-4 position of the heterocyclic nitrogen ring, and particularly preferably by addition of a cis- or trans-hydroxyl group or a cis- or trans-sulphydryl group at the C4 position, and wherein the C-terminus amide group preferably remains unmodified, which can be represented by formula (1b):

$$R^1\text{-Pro}^1\text{-AA}^1\text{-Gly-NH}_2 \tag{1b}$$

wherein Pro$^1$, AA$^1$ and R$^1$ are as described above for formula (1). Preferred compositions of the tripeptides of formula (1b) are:

cis- or trans-4-OH-Pro-D-Arg-Gly-NH$_2$;

cis- or trans-4-OH-Pro-Ile-Gly-NH$_2$;

cis- or trans-4-OH-Pro-Arg-Gly-NH$_2$;

cis- or trans-4-OH-Pro-Trp-Gly-NH$_2$;

and, cis- or trans-4-thio-Pro-Leu-Gly-NH$_2$.

A third group of preferred compositions of the tripeptides of formula (1) which may be utilized alone or in combination with other peptides disclosed herein to treat patients suffering from physiological, psychosomatic, neurological or psychiatric disorders are characterized by optional replacement of Leu, optional modification of the C-terminus amide group, optional modification of the C-terminus hydrogen atom at the nitrogen comprising the peptide bond between Leu-Gly, and by having the N-terminus heterocy clic nitrogen ring of $Pro^1$ remain unmodified, which can be represented by formula (1c). Formula (1c) is depicted as:

$$Pro^1\text{-}AA^1\text{-}NR^2\text{---}CH_2\text{---}R \qquad (1c)$$

wherein $Pro^1$, $AA^1$, and R and $R^2$ are as described above for formula (1), with the proviso that where $Pro^1$ is Pro and $AA^1$ is Leu, $R^2$ cannot be hydrogen when R is either a carboxyl group or a hydroxyalkyl group, and with the further proviso that when $Pro^1$ is Pro and $AA^1$ is Trp, $R^2$ is not hydrogen when R is a hydroxyalkyl group. Preferred compositions of the tripeptides of formula (1c) are:

$$Pro\text{-}Leu\text{-}N(CH_3)CH_2\text{-}CONH_2;$$

and, $$Pro\text{-}Trp\text{-}NHCH_2\text{---}CO_2H.$$

In another embodiment of the invention, additional tripeptides are characterized by replacement of Leu with Arg or D-Arg; replacement of Gly with Ala; optional replacement of Pro with dehydro-Pro, preferably 3,4-dehydro-Pro; optional modification of the C-terminus amide group with a functional group selected from a carboxyl group, a hydroxyalkyl group, preferably a hydroxymethyl group, an alkoxycarbonyl group, and an alkylated carbamyl group; optional modification of the N-terminus heterocyclic nitrogen ring of $Pro^1$ with a substituent selected from a lower alkyl group preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group; and an alkylamino group or a dialkylamino group, preferably a methyl or ethyl amino or dimethyl or diethyl amino group; and/or optional modification of the hydrogen atoms at the nitrogen atoms of the amino acid peptide bonds with a lower alkyl group, preferably having 1 to 3 carbon atoms. This embodiment includes peptides represented by the following formula (2):

$$R^1\text{-}Pro^1\text{-}AA^1\text{-}Ala\text{-}R \qquad (2)$$

and pharmaceutically acceptable salts thereof, where $Pro^1$ represents the amino acid Pro or dehydro-Pro, preferably 3,4-dehydro Pro; $AA^1$ represents an amino acid of the group of Arg or D-Arg; R represents a carboxyl group, a hydroxyalkyl group, a carbamyl group, an alkylcarbamyl group, or an alkoxycarbonyl; and, $R^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

Exemplary preferred tripeptides of formula (2) which may be utilized alone or in combination with other peptides disclosed herein to treat patients suffering from physiological, psychosomatic, neurological or psychiatric disorders are characterized by replacement of the Leu and Gly in Pro-Leu-Gly-$NH_2$, and by the N-terminus $Pro^1$ residue and C-terminus amide remain unmodified, which can be represented by formula (2a). Formula (2a) is depicted as:

$$Pro^1\text{-}AA^1\text{-}Ala\text{-}NH_2 \qquad (2a)$$

wherein $Pro^1$ and $AA^1$ are as described above for formula (2). Preferred tripeptides of formula (2a) are:

$$Pro\text{-}Arg\text{-}Ala\text{-}NH_2;$$

and, $$Pro\text{-}D\text{-}Arg\text{-}Ala\text{-}NH_2.$$

In further embodiments, the small tripeptides are characterized by replacement of Leu with Orn; replacement of Gly with Tyr; optional replacement of Pro with dehydro-Pro, preferably 3,4-dehydro-Pro; optional modification of the C-terminus amide group with a substituent selected from the group of a carboxyl group, a hydroxyalkyl group, preferably hydroxymethyl, an alkoxycarbonyl group, or an alkylated carbamyl group; optional modification of the N-terminus heterocyclic nitrogen ring of $Pro^1$ with a substituent selected from lower alkyl groups, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group, or an alkylamino group or a dialkylamino group, preferably a methyl or ethylamino or a dimethyl or diethylamino group; and/or optional modification of the hydrogen atoms at the nitrogen atoms of the amino acid peptide bonds with a lower alkyl group, preferably having 1 to 3 carbon atoms. Such tripeptides or pharmaceutically acceptable salts thereof can be represented by formula (3):

$$R^1\text{-}Pro^1\text{-}AA^1\text{-}Tyr\text{-}R \qquad (3)$$

where $Pro^1$ represents the amino acid Pro or dehydro-Pro, preferably 3,4-dehydro Pro; $AA^1$ represents the amino acid Orn; R represents a carboxyl group, a hydroxyalkyl group, a carbamyl group, an alkylcarbamyl group, or an alkoxycarbonyl group; and, $R^1$ represents a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or a dimethyl or diethylamino group.

The following paragraphs disclose compositions of the tripeptides of formula (3), which may be utilized alone or in combination with other peptides disclosed herein to treat patients suffering from physiological, psychosomatic, neurological or psychiatric disorders.

Tripeptides of formula (3) that may be utilized alone or in combination with other peptides disclosed herein to treat patients suffering from physiological, psychosomatic, neurological or psychiatric disorders, and that are characterized by replacement of Leu and Gly, optional modification of the N-terminus heterocyclic nitrogen ring of $Pro^1$, and by having the C-terminus amide remain unmodified, can be represented by formula (3a):

$$R^1\text{-}Pro^1\text{-}AA^1\text{-}Tyr\text{-}NH_2 \qquad (3a)$$

where $Pro^1$, $AA^1$ and $R^1$ are as described for formula (3). Preferred tripeptides of formula (3a) are:

$$Pro\text{-}Orn\text{-}Tyr\text{-}NH_2;$$

and $$cis\text{- or }trans\text{-}4\text{-}OH\text{-}Pro\text{-}Orn\text{-}Tyr\text{-}NH_2.$$

In yet another embodiment, the peptides are tetrapeptides characterized by either addition of a C-terminus amino acid of Trp or Tyr to Gly or addition of a N-terminus amino acid of Trp or Phe to Pro to Pro-Leu-Gly-NH$_2$; optional replacement of Leu with Ile, Arg, D-Arg, or Trp; optional replacement of Pro with dehydro-Pro, preferably 3,4-dehydro-Pro; optional modification of the C-terminus amide with a substituent selected from the group of a carboxyl group, a hydroxyalkyl group, preferably a hydroxymethyl group, an alkoxycarbonyl group, or an alkylated carbamyl group; optional modification of the heterocyclic nitrogen rings of Pro$^1$ and Trp and optional modification of the aromatic ring of Phe with a substituent selected from the group of a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or a dialkylamino group, preferably a methyl or ethylamino or a dimethyl or diethylamino group; and/or optional modification of the hydrogen atoms at the nitrogen atoms of the amino acid peptide bonds with a lower alkyl group, preferably having 1 to 3 carbon atoms.

One embodiment of the tetrapeptides or pharmaceutically acceptable salts thereof including a C-terminus amino acid addition can be represented by the following formula (4):

$$R^1\text{-Pro}^1\text{-AA}^1\text{-Gly-AA}^2\text{-R} \tag{4}$$

where Pro$^1$ represents the amino acid Pro or dehydro-Pro, preferably 3,4-dehydro Pro; AA$^1$ represents an amino acid of the group of Ile, Leu, Arg, D-Arg or Trp; AA$^2$ represents Trp or Tyr; R represents a carboxyl group, hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a dehydro group, a halogen atom, preferably a fluorine or chlorine atom, a hydroxyl group, a sulphydryl group, or an alkylamino or dialkylamino group, preferably a methyl or ethylamino or dimethyl or diethylamino group.

Preferred tetrapeptides of formula (4) that may be utilized alone or in combination with other peptides disclosed herein to treat patients suffering from physiological, psychosomatic, neurological or psychiatric disorders are characterized by addition of Trp or Tyr to the C-terminus Gly, by optional replacement of Leu, by optional modification of the N-terminus heterocyclic nitrogen ring of Pro$^1$, and by having the C-terminus amide remain unmodified, which can be represented by formula (4a):

$$R^1\text{-Pro-AA}^1\text{-Gly-AA}^2\text{-NH}_2 \tag{4a}$$

wherein Pro$^1$, AA$^1$, AA$^2$, and R$^1$ are as described for formula (4). Preferred tetrapeptides of formula (4a) are:

cis- or trans-4-OH-Pro-Leu-Gly-Trp-NH$_2$; (SEQ ID NO:1)

cis- or trans-4-OH-Pro-Ile-Gly-Trp-NH$_2$; (SEQ ID NO:2)

cis- or trans-4-OH-Pro-D-Arg-Gly-Trp-NH$_2$; and, 3,4-dehydro-Pro-D-Arg-Gly-Trp-NH$_2$.

Another preferred tetrapeptide of formula (4a) is 3,4-dehydro-Pro-Arg-Gly-Trp-NH$_2$ (SEQ ID NO:62).

Alternative preferred tetrapeptides of formula (4) that may be utilized alone or in combination with other peptides disclosed herein to treat patients suffering from physiological, psychosomatic, neurological or psychiatric disorders are characterized by addition of Trp or Tyr to the C-terminus Gly, by optional replacement of Leu, and by having the N-terminus heterocyclic nitrogen ring of Pro$^1$ remain unmodified, which can be represented by formula (4b):

$$\text{Pro}^1\text{-AA}^1\text{-Gly-AA}^2\text{-NH}_2 \tag{4b}$$

wherein Pro$^1$, AA$^1$ and AA$^2$ are as described for formula (4). Preferred compositions of the tetrapeptides of formula (4b) are:

| | |
|---|---|
| Pro-Ile-Gly-Trp-NH$_2$; | (SEQ ID NO:3) |
| 3,4-dehydro-Pro-Ile-Gly-Trp-NH$_2$; | (SEQ ID NO:4) |
| Pro-Leu-Gly-Trp-NH$_2$; | (SEQ ID NO:5) |
| Pro-Leu-Gly-Tyr-NH$_2$; | (SEQ ID NO:6) |
| Pro-Arg-Gly-Trp-NH$_2$; | (SEQ ID NO:7) |
| Pro-Trp-Gly-Trp-NH$_2$; | (SEQ ID NO:8) |
| Pro-D-Arg-Gly-Trp-NH$_2$; and, | |
| Pro-Ile-Gly-Tyr-NH$_2$. | (SEQ ID NO:9) |

Another embodiment of the tetrapeptide compositions or pharmaceutically acceptable salt thereof including a N-terminus amino acid addition can be represented by formula (5):

$$R^1\text{-AA}^1\text{-R}^2\text{-Pro}^1\text{-AA}^2\text{-Gly-R} \tag{5}$$

where Pro$^1$ represents the amino acid Pro or dehydro-Pro, preferably 3,4-dehydro Pro; AA$^1$ represents an amino acid of the group of Trp, Tyr, or Phe; AA$^2$ represents an amino acid of the group of Leu, Ile, or Trp; R represents a carboxyl group, hydroxyalkyl group, a carbamyl group, an alkylcarbamyl group, or an alkoxycarbonyl group; and, R$^1$ and R$^2$ each independently represent a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

In some preferred embodiments, tetrapeptides of formula (5) are used in combination with one or more other peptides disclosed herein.

Exemplary tetrapeptides of formula (5) that may be utilized alone or in combination with other peptides disclosed herein to treat patients suffering from physiological, psychosomatic, neurological or psychiatric disorders are characterized by addition of Trp, Tyr, or Phe to the N-terminus Pro$^1$, optional replacement of Leu, optional modification of the heterocyclic nitrogen rings of Pro$^1$ and Trp and optional modification of the aromatic ring of Phe and Tyr, and wherein the C-terminus amide remains unmodified, which can be represented by formula (5a):

$$R^1\text{-AA}^1\text{-R}^2\text{-Pro}^1\text{-AA}^2\text{-Gly-NH}_2 \tag{5a}$$

wherein Pro$^1$, AA$^1$, AA$^2$, R$^1$, and R$^2$ are as described for formula (5), with the proviso that where Pro$^1$ is Pro, R$^1$ and R$^2$ cannot both be a hydrogen atom when AA$^1$ is Tyr and AA$^2$ is Trp, since Tyr-Pro-Trp-Gly-NH$_2$ (SEQ ID NO: 54 is a known compound, and with the further proviso that where Pro$^1$ is Pro and AA$^2$ is Leu, R$^1$ and R$^2$ cannot both be a hydrogen atom when AA$^1$ is Phe or Tyr. Preferred compositions of the tetrapeptides of formula (5a) are:

Trp-Pro-Leu-Gly-NH$_2$;  (SEQ ID NO:10)

Phe-Pro-Leu-Gly-NH$_2$;  (SEQ ID NO:11)

4-F-Phe-Pro-Leu-Gly-NH$_2$;  (SEQ ID NO:12)

4-Cl-Phe-Pro-Leu-Gly-NH$_2$;  (SEQ ID NO:13)

4-F-Phe-Pro-Ile-Gly-NH$_2$;  (SEQ ID NO:14)

4-F-Phe-cis- or trans-4-OH-Pro-Leu-Gly-NH$_2$;  (SEQ ID NO:15)

4-F-Phe-cis- or trans-4-OH-Pro-Ile-Gly-NH$_2$;  (SEQ ID NO:16)

Trp-Pro-Leu-Gly-NH$_2$;  (SEQ ID NO:17)

Trp-Pro-Ile-Gly-NH$_2$;  (SEQ ID NO:18)

Trp-cis- or trans-4-OH-Pro-Leu-Gly-NH$_2$;  (SEQ ID NO:19)

Trp-cis- or trans-4-OH-Pro-Ile-Gly-NH$_2$.  (SEQ ID NO:20)

An additional preferred tetrapeptide of formula (5a) is

4-Cl-Phe-cis- or trans-4-OH-Pro-Ile-Gly-NH$_2$ (SEQ ID NO:60).

Another group of preferred tetrapeptides of formula (5) that may be utilized alone or in combination with other peptides disclosed herein to treat patients suffering from physiological, psychosomatic, neurological or psychiatric disorders are characterized by addition of Phe to the N-terminus Pro$^1$, optional replacement of Leu with Arg, optional modification of the heterocyclic nitrogen ring of Pro$^1$ and optional modification of the aromatic ring of Phe, and modification of the C-terminus amide to a carbamyl group, which can be represented by formula (5b):

$$R^1\text{-}AA^1\text{-}R^2\text{-}Pro^1\text{-}AA^2\text{-}Gly\text{-}R \tag{5b}$$

wherein Pro$^1$, AA$^1$, AA$^2$, R$^1$, R$^2$ and R are as described for formula (5). Preferred compositions of the tetrapeptides of formula (5b) include, but are not solely limited to, additional optional modification of the N-terminus heterocyclic nitrogen ring of Pro$^1$ with a cis- or trans-4-OH— group; and additional optional modifications at AA$^2$, preferably Arg. A preferred peptide of formula (5b) is 4-F-Phe-cis- or trans-4-OH-Pro-Arg-Gly-1,2,3,4-Tetrahydroisoquinoline-3-carboxamide (SEQ NO:75).

In yet another embodiment of the invention, the peptides are pentapeptides with either addition of two N-terminus amino acids of Phe, Tyr, Leu, or Ile to Pro$^1$, addition of a N-terminus amino acid of Phe or Tyr to Pro$^1$ and a C-terminus amino acid addition of Trp to Gly, or addition of a C-terminus amino acids of Trp to Gly and an internal amino acid between Pro$^1$ and Gly, to Pro-Leu-Gly-NH$_2$; optional replacement of Leu with Ile or Trp; optional replacement of Pro with dehydro-Pro, preferably 3,4-dehydro-Pro; optional modification of the C-terminus amide with a substituent selected from the group of a carboxyl group, a hydroxyalkyl group, preferably a hydroxymethyl group, an alkoxycarbonyl group, or an alkylated carbamyl group; optional modification of the heterocyclic nitrogen ring of Pro$^1$ and optional modification of the aromatic rings of Tyr or Phe with a substituent selected from the group of a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or a dialkylamino group, preferably a methyl or ethylamino or a dimethyl or diethylamino group; and/or optional modification of the hydrogen atoms at the nitrogen atoms of the amino acid peptide bonds with a lower alkyl group, preferably having 1 to 3 carbon atoms.

One embodiment of the pentapeptide compositions including addition of two N-terminus amino acids or pharmaceutically acceptable salt thereof can be represented by formula (6):

$$R^1\text{-}AA^1\text{-}AA^2\text{-}R^2\text{-}Pro^1\text{-}AA^3\text{-}Gly\text{-}R \tag{6}$$

where Pro$^1$ represents the amino acid Pro or dehydro-Pro, preferably 3,4-dehydro Pro; AA$^1$ and AA$^2$ each independently represent an amino acid of the group of Phe or Tyr; AA$^3$ represents an amino acid of the group of Leu or Ile; R represents a carboxyl group, hydroxyalkyl group, a carbamyl group, an alkylcarbamyl group, or an alkoxycarbonyl group; and, R$^1$ and R$^2$ each independently represent a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or dimethyl or diethylamino group.

Preferred pentapeptides of formula (6) that may be utilized alone or in combination with other peptides disclosed herein to treat patients suffering from physiological, psychosomatic, neurological or psychiatric disorders are characterized by addition of two N-terminus amino acids of Phe and Tyr to Pro$^1$, optional modification of the heterocyclic nitrogen ring of Pro$^1$ and optional modification of the aromatic rings of Phe or Tyr, optional replacement of Leu, and by having the C-terminus amide of Gly remain unmodified, which can be represented by formula (6a):

$$R^1\text{-}AA^1\text{-}AA^2\text{-}R^2\text{-}Pro^1\text{-}AA^3\text{-}Gly\text{-}NH_2 \tag{6a}$$

wherein Pro$^1$, AA$^1$, AA$^2$, R$^1$, and R$^2$ are as described for formula (6). Preferred pentapeptides of formula (6a) are:

4-F-Phe-Tyr-Pro-Leu-Gly-NH$_2$;  (SEQ ID NO:21)

4-Cl-Phe-Tyr-Pro-Leu-Gly-NH$_2$;  (SEQ ID NO:22)

Phe-Tyr-Pro-Leu-Gly-NH$_2$;  (SEQ ID NO:23)

Phe-Tyr-Pro-Ile-Gly-NH$_2$;  (SEQ ID NO:24)

Phe-Tyr-cis- or trans-4-OH-Pro-Leu-Gly-NH$_2$;  (SEQ ID NO:25)

(SEQ ID NO:26)

```
                                                      -continued
Phe-Tyr-cis- or trans-4-OH-Pro-Ile-Gly-NH2;

(SEQ ID NO:27)
Tyr-Tyr-Pro-Leu-Gly-NH2;

(SEQ ID NO:28)
Tyr-Tyr-Pro-Ile-Gly-NH2;

(SEQ ID NO:29)
Tyr-Tyr-cis- or trans-4-OH-Pro-Leu-Gly-NH2; and, (SEQ ID NO:30)
Tyr-Tyr-cis- or trans-4-OH-Pro-Ile-Gly-NH2.
```

Another embodiment of the invention provides pentapeptide compositions or pharmaceutically acceptable salts thereof including addition of both a N-terminus amino acid and a C-terminus amino acid represented by formula (7):

$$R^1\text{-}AA^1\text{-}R^2\text{-}Pro^1\text{-}AA^2\text{-}Gly\text{-}AA^3\text{-}R \quad (7)$$

where $Pro^1$ represents the amino acid Pro or dehydro-Pro, preferably 3,4-dehydro Pro; $AA^1$ represents an amino acid of the group of Phe or Tyr; $AA^2$ represents an amino acid of the group of Leu, Ile, Arg, D-Arg, or Trp; $AA^3$ represents the amino acid Trp; R represents a carboxyl group, hydroxyalkyl group, a carbamyl group, an alkylcarbamyl group, or an alkoxycarbonyl group; and, $R^1$ and $R^2$ each independently represent a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or dimethyl or diethylamino group.

Preferred pentapeptides of formula (7) which may be utilized alone or in combination with other peptides disclosed herein to treat patients suffering from physiological, psychosomatic, neurological or psychiatric disorders are characterized by addition of a N-terminus amino acid of Phe or Tyr to $Pro^1$, addition of a C-terminus amino acid of Trp to Gly, optional modification of the heterocyclic nitrogen ring of $Pro^1$ and optional modification of the aromatic rings of Phe or Tyr, optional replacement of Leu with Ile, Arg, D-Arg, or Trp, and the C-terminus amide remaining unmodified, and can be represented by formula (7a):

$$R^1\text{-}AA^1\text{-}R^2\text{-}Pro^1\text{-}AA^2\text{-}Gly\text{-}Trp\text{-}NH_2 \quad (7a)$$

wherein $Pro^1$, $AA^1$, $AA^2$, $R^1$, and $R^2$ are as described for formula (7). Preferred pentapeptides of formula (7a) are:

```
                                   (SEQ ID NO:31)
Phe-Pro-Leu-Gly-Trp-NH2;

(SEQ ID NO:32)
Tyr-Pro-Leu-Gly-Trp-NH2;

(SEQ ID NO:33)
Phe-cis- or trans-4-OH-Pro-Leu-Gly-Trp-NH2;

(SEQ ID NO:34)
Phe-Pro-Ile-Gly-Trp-NH2;

(SEQ ID NO:35)
Phe-cis- or trans-4-OH-Pro-Ile-Gly-Trp-NH2;

(SEQ ID NO:36)
```

```
                                      -continued
Tyr-cis- or trans-4-OH-Pro-Leu-Gly-Trp-NH2;

(SEQ ID NO:37)
Tyr-Pro-Ile-Gly-Trp-NH2;

(SEQ ID NO:38)
Tyr-cis- or trans-4-OH-Pro-Leu-Gly-Trp-NH2;

(SEQ ID NO:39)
Tyr-Pro-Trp-Gly-Trp-NH2;

(SEQ ID NO:40)
Tyr-cis- or trans-4-OH-Pro-Trp-Gly-Trp-NH2;

(SEQ ID NO:41)
4-F-Phe-cis- or trans-4-OH-Pro-Ile-Gly-Trp-NH2;

(SEQ ID NO:42)
4-F-Phe-cis- or trans-4-OH-Pro-Leu-Gly-Trp-NH2;

(SEQ ID NO:43)
4-F-Phe-cis- or trans-4-OH-Pro-Arg-Gly-Trp-NH2;
and,

4-F-Phe-cis- or trans-4-OH-Pro-D-Arg-Gly-Trp-NH2.
```

Additional preferred pentapeptides of formula (7a) include:

```
                                   (SEQ ID NO:66)
3-F-Phe-cis- or trans-4-OH-Pro-Arg-Gly-Trp-NH2;

(SEQ ID NO:68)
2-F-Phe-cis- or trans-4-OH-Pro-Arg-Gly-Trp-NH2;
and (SEQ ID NO:61)
4-Cl-Phe-cis- or trans-4-OH-Pro-Arg-Gly-Trp-NH2.
```

An additional group of preferred pentapeptides of formula (7a) is characterized by the optional modification of $Pro^1$ to dehydro-Pro, preferably 3,4-dehydro-Pro, and includes:

```
                                   (SEQ ID NO:72)
4-F-Phe-3,4-dehydro-Pro-Ile-Gly-Trp-NH2; and (SEQ ID NO:55)
4-F-Phe-3,4-dehydro-Pro-Arg-Gly-Trp-NH2.
```

Further embodiments encompassed within formula (7a) include compounds having additional optional modifications at $AA^2$, preferably Arg, His, Homo-Arg, L-Allo-Ile, or canavanine; additional optional modifications at $R^1$ and/or $R^2$ (preferably $R^1$) and preferably an amino group, a carboxyl group, a nitro group, or a phosphono group (preferably as phosphono-Tyr); additional optional modification of the heterocyclic nitrogen ring of $Pro^1$, preferably cis- or trans-4-OH or Homo-Pro. Additional preferred peptides of formula (7a) are:

| | |
|---|---|
| 4-NH₂-Phe-cis- or trans-4-OH-Pro-Arg-Gly-Trp-NH₂; | (SEQ ID NO:63) |
| 4-F-Phe-cis- or trans-4-OH-Pro-His-Gly-Trp-NH₂; | (SEQ ID NO:64) |
| 4-NO₂-Phe-cis- or trans-4-OH-Pro-Arg-Gly-Trp-NH₂; | (SEQ ID NO:65) |
| 4-CH₃O-Phe-cis- or trans-4-OH-Pro-Arg-Gly-Trp-NH₂; | (SEQ ID NO:59) |
| 4-F-Phe-cis- or trans-4-OH-Pro-Homo-Arg-Gly-Trp-NH₂; | (SEQ ID NO:71) |
| 4-F-Phe-Homo-Pro-Ile-Gly-Trp-NH₂; | (SEQ ID NO:69) |
| 4-F-Phe-Homo-Pro-Arg-Gly-Trp-NH₂; and, | (SEQ ID NO:57) |
| 4-F-Phe-cis- or trans-4-OH-Pro-L-Allo-Ile-Gly-Trp-NH₂. | (SEQ ID NO:73) |

Preferred pentapeptides of formula (7) which may be utilized alone or in combination with other peptides disclosed herein to treat patients suffering from physiological, psychosomatic, neurological or psychiatric disorders are characterized by addition of an N-terminus amino acid of Phe; addition of a C-terminus amino acid of Trp to Gly; optional modification of the heterocyclic nitrogen ring of Pro¹ and optional modification of the aromatic ring of Phe; and by the C-terminus amide remaining unmodified, and can be represented by formula (7b):

$$R^1\text{-}AA^1\text{-}R^2\text{-}Pro^1\text{-}AA^2\text{-}Gly\text{-}Trp\text{-}NH_2 \quad (7b)$$

wherein $AA^1$ is Phe; and $Pro^1$, $AA^2$, $R^1$ and $R^2$ are as described for formula (7) with the following additional optional modification of the N-terminus heterocyclic nitrogen ring of $Pro^1$ with a substituent selected from the group consisting of cis-4-OH—, trans-4-OH—, cis-3-OH—, and trans-3-OH—; and additional optional modifications at $R^1$, preferably two or more halogen atoms or a cyano group. Preferred pentapeptides of formula (7b) include:

| | |
|---|---|
| 3,4-Dichloro-Phe-cis- or trans-4-OH-Pro-Arg-Gly-Trp-NH₂; | (SEQ NO:76) |
| 4-NC-Phe-cis- or trans-4-OH-Pro-Arg-Gly-Trp-NH₂; | (SEQ NO:77) |
| 4-F-Phe-cis- or trans-4-OH-Pro-D-Leu-Gly-Trp-NH₂; and, | (SEQ NO:78) |
| 4-F-Phe-trans-3-Hydroxy-Pro-Arg-Gly-Trp-NH₂. | (SEQ NO:79) |

Additional preferred pentapeptides of formula (7) that may be utilized alone or in combination with other peptides disclosed herein to treat patients suffering from physiological, psychosomatic, neurological or psychiatric disorders are characterized by addition of an N-terminus amino acid of Phe, addition of a C-terminus amino acid of Trp to Gly, optional modification of the heterocyclic nitrogen ring of Pro¹ and optional modification of the aromatic ring of Phe, and the absence of the C-terminus amide, which can be represented by formula (7c):

$$R^1\text{-}AA^1\text{-}R^2\text{-}Pro^1\text{-}AA^2\text{-}Gly\text{-}Trp \quad (7c)$$

where $Pro^1$, $AA^1$, $AA^2$, $R^1$ and $R^2$ are as described for formula (7) with additional optional modifications at $AA^2$, preferably Homo-Arg; and additional optional modification of the N-terminus heterocyclic nitrogen ring of $Pro^1$ with a substituent selected from the group consisting of cis-4-OH—, trans-4-OH—, cis-3-OH— and trans-3-OH. A preferred peptide of formula (7c) is 4-F-Phe-cis- or trans-4-OH-Pro-Homo-Arg-Gly-Trp (SEQ NO:74).

Another group of preferred pentapeptides of formula (7) that may be utilized alone or in combination with other peptides disclosed herein to treat patients suffering from physiological, psychosomatic, neurological or psychiatric disorders are characterized by addition of an N-terminus amino acid of Phe, Tyr or PhenylGly; addition of a C-terminus amino acid of Trp or AzaTrp to Gly; optional modification of the N-terminus heterocyclic nitrogen ring of Pro¹ and optional modification of the aromatic rings of Phe, Tyr and PhenylGly; and additional optional modification at R, preferably a hydroxyamino group, which can be represented by formula (7d):

$$R^1\text{-}AA^1\text{-}R^2\text{-}Pro^1\text{-}AA^2\text{-}Gly\text{-}AA^3\text{-}R \quad (7d)$$

wherein $Pro^1$, $AA^1$, $AA^2$, $AA^3$, $R^1$, $R^2$ and R are as described for formula (7) with the following additional optional modifications at $Pro^1$, preferably Homo-Pro; additional optional modifications at $AA^1$, preferably PhenylGly; additional optional modifications at $AA^3$, preferably AzaTrp; additional optional modifications at $R^1$, preferably two or more halogen atoms, a haloform, or a methoxyl group; additional optional modifications at $R^2$, preferably a cis- or trans-3-OH— group; and additional optional modifications at R, preferably a hydroxyamino group. Preferred pentapeptides of formula (7d) include:

| | |
|---|---|
| 4-CH₃O-Phe-3,4-Dehydro-Pro-Arg-Gly-Trp-NH₂; | (SEQ NO:81) |
| 2,4-Di-F-Phe-3,4-Dihydro-Pro-Arg-Gly-Trp-NH₂; | (SEQ NO:82) |
| 4-CF₃-Phe-3,4-Dehydro-Pro-Arg-Gly-Trp-NH₂; | (SEQ NO:83) |
| 4-F-PhenylGly-3,4-Dehydro-Pro-Arg-Gly-Trp-NH₂; | (SEQ NO:84) |
| 3-F-Tyr-3,4-Dehydro-Pro-Arg-Gly-Trp-NH₂; | (SEQ NO:85) |
| 4-F-Phe-3,4-Dehydro-Pro-Arg-Gly-Trp-NHOH; | (SEQ NO:86) |
| | (SEQ NO:87) |

-continued 3,4-Di-Cl-Phe-3,4-Dihydro-Pro-Arg-Gly-Trp-NH$_2$;

(SEQ NO:88)
2-F-Tyr-3,4-Dehydro-Pro-Arg-Gly-Trp-NH$_2$; and, (SEQ NO:89)
4-F-Phe-3,4-Dehydro-Pro-Arg-Gly-7-AzaTrp-NH$_2$.

Another group of preferred pentapeptides of formula (7) which may be utilized alone or in combination with other peptides disclosed herein to treat patients suffering from physiological, psychosomatic, neurological or psychiatric disorders are characterized by addition of an N-terminus amino acid of Phe; addition of a C-terminus amino acid of Trp to Gly; optional modification of the heterocyclic nitrogen ring of Pro$^1$ and optional modification of the aromatic rings of Phe and Trp; and by having the C-terminus amide remain unmodified, which can be represented by formula (7e):

$$R^1\text{-}AA^1\text{-}R^2\text{-}Pro^1\text{-}AA^2\text{-}Gly\text{-}R^4\text{-}Trp\text{-}NH_2 \tag{7e}$$

wherein Pro$^1$, AA$^1$, AA$^2$, R$^1$ and R$^2$ are as described for formula (7) with the following additional optional modification of the N-terminus heterocyclic nitrogen ring of Pro$^1$ with a substituent selected from the group consisting of cis-4-OH—, trans-4-OH—, cis-3-OH—, and trans-3-OH—; and R$^4$ represents a modification of the tryptophan residue at one of C4, C5, C6 and C7 with a halogen atom, a hydroxyl group, or an alkyl group. Preferred pentapeptides of formula (7e) include:

4-F-Phe-cis- or trans-4-OH-Pro-Arg-Gly-4-F-Trp-NH$_2$ (SEQ NO:107); and,

4-F-Phe-cis- or trans-4-OH-Pro-Arg-Gly-7-Methyl-Trp-NH$_2$ (SEQ NO:108).

Another group of preferred compositions of the pentapeptides of formula (7) which may be utilized alone or in combination with other peptides disclosed herein to treat patients suffering from physiological, psychosomatic, neurological or psychiatric disorders are characterized by addition of an N-terminus amino acid of Phe; addition of a C-terminus amino acid of Trp to Gly; optional modification of the heterocyclic nitrogen ring of Pro$^1$ and optional modification of the aromatic rings of Phe and Leu; and by having the C-terminus amide remain unmodified, which can be represented by formula (7f):

$$R^1\text{-}AA^1\text{-}R^2\text{-}Pro^1\text{-}R^5\text{-}AA^2\text{-}Gly\text{-}Trp\text{-}NH_2 \tag{7f}$$

wherein Pro$^1$, AA$^1$, AA$^2$, R$^1$ and R$^2$ are as described for formula (7) with the following additional optional modification of the N-terminus heterocyclic nitrogen ring of Pro$^1$ with a substituent selected from the group consisting of cis-4-OH—, trans-4-OH—, cis-3-OH—, and trans-3-OH—; and R$^5$ represents at least one halogen atom. A preferred composition of the pentapeptides of formula (7f) is 4-F-Phe-4-OH-Pro-5,5,5-Trifluoro-Leu-Gly-Trp-NH$_2$ (SEQ NO:109).

Another group of preferred pentapeptides of formula (7) which may be utilized alone or in combination with other peptides disclosed herein to treat patients suffering from physiological, psychosomatic, neurological or psychiatric disorders are characterized by addition of an N-terminus amino acid of Phe; addition of a C-terminus amino acid of Trp to Gly; additional optional modifications at Pro$^1$, preferably Homo-Pro; optional modification of the heterocyclic nitrogen ring of Pro$^1$ and optional modification of the aromatic rings of Phe and Trp; and by having the C-terminus amide remain unmodified, which can be represented by formula (7g):

$$R^1\text{-}AA^1\text{-}R^2\text{-}Pro^1\text{-}AA^2\text{-}Gly\text{-}R^4\text{-}AA^3\text{-}R \tag{7g}$$

wherein Pro$^1$, AA$^1$, AA$^2$, AA$^3$, R$^1$, R$^2$ and R are as described for formula (7) with the following additional optional modifications at Pro$^1$, preferably Homo-Pro or 3,4-dihydro-Pro; additional optional modifications at R$^2$, preferably cis- or trans-3-OH— group; and R$^4$ represents a halogen atom, a methyl group, a methoxyl group or a hydroxyl group. Preferred pentapeptides of formula (7g) include:

(SEQ NO:90)
4-F-Phe-3,4-Dehydro-Pro-Arg-Gly-4-F-Trp-NH$_2$ (SEQ NO:91)
4-F-Phe-3,4-Dehydro-Pro-Arg-Gly-5-F-Trp-NH$_2$ (SEQ NO:92)
4-F-Phe-3,4-Dihydro-Pro-Arg-Gly-6-F-Trp-NH$_2$ (SEQ NO:93)
4-F-Phe-3,4-Dehydro-Pro-Arg-Gly-3-CH$_3$O-Trp-NH$_2$ (SEQ NO:94)
4-F-Phe-3,4-Dehydro-Pro-Arg-Gly-N-Methyl-Trp-NH$_2$ (SEQ NO:95)
4-F-Phe-3,4-Dehydro-Pro-Arg-Gly-1-Methyl-Trp-NH$_2$ (SEQ NO:96)
4-F-Phe-3,4-Dehydro-Pro-Arg-Gly-4-Methyl-Trp-NH$_2$ (SEQ NO:97)
4-F-Phe-3,4-Dehydro-Pro-Arg-Gly-5-Methyl-Trp-NH$_2$ (SEQ NO:98)
4-F-Phe-3,4-Dehydro-Pro-Arg-Gly-6-Methyl-Trp-NH$_2$ (SEQ NO:99)
4-F-Phe-3,4-Dehydro-Pro-Arg-Gly-5-Hydroxy-Trp-NH$_2$.

In yet another embodiment of the invention, pentapeptide compositions or pharmaceutically acceptable salts thereof including addition of a C-terminus amino acid and an internal amino acid can be represented by the following formula (8):

$$R^1\text{-}Pro^1\text{-}AA^1\text{-}AA^2\text{-}Gly\text{-}AA^3\text{-}R \tag{8}$$

where Pro$^1$ represents the amino acid Pro or dehydro-Pro, preferably 3,4-dehydro-Pro; AA$^1$ and AA$^2$ each independently represent an amino acid of the group of Leu or Ile; AA$^3$ represents Trp; R represents a carboxyl group, a hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino group or dimethyl or diethylamino group.

Preferred compositions of the pentapeptides of formula (8) which may be utilized alone or in combination with other peptides disclosed herein to treat patients suffering from physiological, psychosomatic, neurological or psychiatric disorders are characterized by addition of a C-terminus amino acid of Trp to Gly, addition of an internal amino acid of Leu or Ile between Pro$^1$ and Gly, optional modification of the heterocyclic nitrogen ring of Pro¹, optional replacement of Leu with Ile, and by having the C-terminus amide remain unmodified, which can be represented by formula (8a):

$$R^1\text{-Pro}^1\text{-AA}^1\text{-AA}^2\text{-Gly-Trp-NH}_2 \quad (8a)$$

wherein Pro¹, AA¹, AA², and R¹ are as described for formula (8). Preferred pentapeptides of formula (8a) are:

Pro-Ile-Leu-Gly-Trp-NH₂ (SEQ ID NO: 44), and, cis- or trans-4-OH-Pro-Ile-Leu-Gly-Trp-NH₂ (SEQ ID NO:45).

In another embodiment of the invention, pentapeptide compositions or pharmaceutically acceptable salts thereof including addition of both a N-terminus amino acid and a C-terminus amino acid can be represented by the following formula (9):

$$R^1\text{-AA}^1\text{-R}^2\text{-Pro}^1\text{-AA}^2\text{-Gly-AA}^3\text{-R} \quad (9)$$

where Pro¹ represents the amino acid Pro or dehydro-Pro, preferably 3,4-dehydro Pro; AA¹ represents the amino acid Ala; AA² represents an amino acid of the group of Leu, Ile, Arg, D-Arg, Trp, or canavanine; AA³ represents the amino acid Trp; R represents a carboxyl group, hydroxyalkyl group, a carbamyl group, an alkylcarbamyl group, or an alkoxycarbonyl group; and, R¹ represents a pyridyl ring, preferably as a 3-(3-pyridyl) moiety; R² represents a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or dimethyl or diethylamino group.

A preferred composition of formula (9) includes but is not limited to:

3-(3-pyridyl)-Ala-4-OH-Pro-Arg-Gly-Trp-NH₂ (SEQ ID NO:70).

In another embodiment of the invention, hexapeptide compositions or pharmaceutically acceptable salts thereof including addition of both a N-terminus amino acid and a C-terminus amino acid can be represented by formula (10):

$$R^1\text{-AA}^1\text{-R}^2\text{-Pro}^1\text{-AA}^2\text{-AA}^4\text{-Gly-AA}^3\text{-R} \quad (10)$$

where Pro¹ represents the amino acid Pro or dehydro-Pro; AA¹ represents an amino acid of the group of Phe or Tyr; AA² represents an amino acid of the group of Leu, Ile, Arg, D-Arg, Trp, or canavanine; AA³ represents the amino acid Trp; AA⁴ represents the amino acid Gly or Ile; R represents a carboxyl group, hydroxyalkyl group, a carbamyl group, an alkylcarbamyl group, or an alkoxycarbonyl group; and, R¹ and R² each independently represent a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or dimethyl or diethylamino group.

A preferred composition of formula (10) is 4-F-Phe-3,4-Dehydro-Pro-Arg-Gly-Gly-Trp-NH₂ (SEQ NO:80).

Preferred hexapeptides of formula (10) which may be utilized alone or in combination with other peptides disclosed herein to treat patients suffering from physiological, psychosomatic, neurological or psychiatric disorders are characterized by addition of a C-terminus amino acid of Trp, optional modification of the heterocyclic nitrogen ring of Pro¹, preferably a cis- or trans-4-OH group, a fluorine atom at position 4 of Phe; preferably Arg at AA²; Tpr at AA³; and Ile or Gly at AA⁴, and by having the C-terminus amide remain unmodified, which can be represented by formula (10a):

$$R^1\text{-Phe-R}^2\text{-Pro}^1\text{-AA}^2\text{-AA}^4\text{-Gly-Trp-NH}_2 \quad (10a)$$

wherein preferred peptides of formula (10a) are:

(SEQ ID NO:58)
4-F-Phe-4-OH-Pro-Arg-Gly-Gly-Trp-NH₂; and (SEQ ID NO:67)
4-F-Phe-4-OH-Pro-Arg-Ile-Gly-Trp-NH₂.

In another embodiment of the invention, heptapeptide compositions or pharmaceutically acceptable salts thereof including addition of both a N-terminus amino acid and a C-terminus amino acid can be represented by the following formula (11):

$$R^1\text{-AA}^1\text{-R}^2\text{-Pro}^1\text{-AA}^2\text{-AA}^4\text{-AA}^5\text{-Gly-AA}^3\text{-R} \quad (11)$$

where Pro¹ represents the amino acid Pro or dehydro-Pro; AA¹ represents an amino acid of the group of Phe or Tyr; AA² represents an amino acid of the group of Leu, Ile, Arg, D-Arg, Trp, or canavanine; AA³ represents the amino acid Trp; AA⁴ and AA⁵ represent the amino acid Gly or Ile; R represents a carboxyl group, hydroxyalkyl group, a carbamyl group, an alkylcarbamyl group, or an alkoxycarbonyl group; and, R¹ and R² each independently represent a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio- group, or an alkylamino or dialkylamino group, preferably a methyl or ethylamino or dimethyl or diethylamino group, or a phosphono group (preferably as phosphono-Tyr).

A preferred composition of formula (11) is:

4-F-Phe-4-OH-Pro-Arg-Gly-Ile-Gly-Trp-NH₂ (SEQ ID NO:56).

Preferred tetrapeptides of formula (12) or pharmaceutically acceptable salts thereof which may be utilized alone or in combination with other peptides disclosed herein to treat patients suffering from physiological, psychosomatic, neurological or psychiatric disorders are characterized by replacement of Pro with Arg; addition of an N-terminus amino acid of Phe to Arg; addition of a C-terminus amino acid of Trp to Gly; optional modification of the aromatic rings of Phe and by having the C-terminus amide remain unmodified, which can be represented by formula (12):

$$R^1\text{-Phe-R}^2\text{-Arg-Gly-Trp-NH}_2 \quad (12)$$

where R¹ represents a halogen atom and R² represents a carboxylic acid of a monocyclic organic compound with a three to six membered ring structure having a hetero nitrogen atom. Preferred compositions of the pentapeptides of formula (12) include, but are not necessarily limited to:

```
4-F-Phe-isonipecotic acid-Arg-Gly-Trp-NH2(4-pyridinecarboxylic acid)    (SEQ NO:100)

4-F-Phe-2-Carboxy-Azetidine-Arg-Gly-Trp-NH2                             (SEQ NO:101)

4-F-Phe-2-carboxy-Aziridine-Arg-Gly-Trp-NH2                             (SEQ NO:103)

4-F-Phe-3-Carboxy-1,4,5,6-Tetrahydropyridine-Arg-Gly-Trp-NH2            (SEQ NO:105)

4-F-Phe-2-Carboxypyrrole-Arg-Gly-Trp-NH2.                               (SEQ NO:106)
```

The following paragraph discloses compositions of the pentapeptides of formula (13), which may be utilized alone or in combination with other peptides disclosed herein to treat patients suffering from physiological, psychosomatic, neurological or psychiatric disorders.

Preferred compositions of the pentapeptides of formula (13) or a pharmaceutically acceptable salt thereof which may be utilized alone or in combination with other peptides disclosed herein to treat patients suffering from physiological, psychosomatic, neurological or psychiatric disorders are characterized by replacement of Pro with Arg; addition of an N-terminus amino acid of Phe to Arg; addition of an internal amino acid; addition of a C-terminus amino acid of Trp to Gly; optional modification of the aromatic ring of Phe and by C-terminus amide remaining unmodified, which can be represented by formula (13). Formula (13) is depicted as:

$$R^1\text{-Phe-AA}^1\text{-Arg-Gly-Trp-NH}_2 \qquad (13)$$

where $AA^1$ represents an amino acid selected from the group comprising 1-amino-1-carboxycyclopentane and 1-amino-1-carboxy-cyclopropyl and $R^1$ represents a halogen atom. Preferred compositions of the pentapeptides of formula (13) include, but are not necessarily limited to, 4-F-Phe-1-Amino-1-Carboxycyclopentane-Arg-Gly-Trp-NH$_2$ (SEQ NO:102) and 4-F-Phe-1-Amino-1-Carboxy-Cyclopropyl-Arg-Gly-Trp-NH$_2$ (SEQ NO:104).

In some embodiments, Gly in compounds of formula (7) through formula (11) may be replaced with Val or Ala. One preferred peptide composition wherein Gly is substituted with Sar in formula (7) is 4-F-Phe-3,4-Dehydro-Pro-Arg-Sar-Trp-NH$_2$ (SEQ NO:110).

In yet another embodiment of the invention, the peptides are polypeptides including chemical combinations and/or overlapping chemical combinations of any of the peptides of any of formula (1) through formula (11) described above which may be utilized alone or in combination with other peptides disclosed herein to treat patients suffering from physiological, psychosomatic, neurological or psychiatric disorders. The chemical combinations and/or overlapping chemical combinations of the peptides disclosed preferably range from at least about three to at least about ten amino acids. Examples of such combinations include: 4-F-Phe-cis- or trans-4-OH-Pro-Ile-Gly-Trp-Gly-NH2 (SEQ ID NO:46); 4-F-Phe-cis or trans-4-OH-Pro-Ile-Gly-Trp-Gly-Trp-NH$_2$ (SEQ ID NO:47); 4-F-Phe-cis- or trans-4-OH-Pro-Leu-Gly-Trp-Gly-NH$_2$ (SEQ ID NO:48); 4-F-Phe-cis- or trans-4-OH-Pro-Leu-Gly-Trp-Gly-Trp-NH$_2$ (SEQ ID NO:49); Pro-Ile-Gly-Trp-Pro-Ile-Gly-NH$_2$; (SEQ ID NO:50) 4-F-Phe-cis- or trans-4-OH-Pro-Arg-Gly-Trp-Gly-NH$_2$ (SEQ ID NO:51); 4-F-Phe-cis or trans-4-OH-Pro-Arg-Gly-Trp-Gly-Trp-NH$_2$ (SEQ ID NO:52); cis- or trans-4-OH-Pro-Ile-Gly-cis- or trans-4-OH-Pro-Ile-Gly-NH$_2$ (SEQ ID NO:53); 3,4-dehydro-Pro-D-Arg-Gly-3,4-dehydro-Pro-D-Arg-Gly-NH$_2$; 3,4-dehydro-Pro-D-Arg-Gly-Trp-Gly-NH$_2$; and 3,4-dehydro-Pro-D-Arg-Gly-Trp-Gly-Trp-NH$_2$.

Especially preferred compositions of the present invention are peptides that show higher activity in the Porsolt swim test than known compounds used to treat anxiety and/or depression. These peptides may vary in length, with the preferred peptides being tetrapeptides, pentapeptides, hexapeptides and heptapeptides. A general formula for these especially preferred peptides, which are disclosed throughout this specification, is:

$$R^1\text{-Phe-Pro}^1\text{-AA}^2\text{-AA}^3\text{-NH}_2,$$

for a tetrapeptide, wherein $R^1$ is preferably a halogen atom, most preferably a fluorine or chlorine atom, a carboxyl group, an amino group or a nitro group, with all modifications preferably at the C4 atom of Phe; $Pro^1$ is 3,4-dehydro Pro, Homo-Pro, cis- or trans-4OH-Pro or Pro, as listed in order of preference, $AA^2$ is preferably Ile, Leu or Arg; and $AA^3$ is preferably Gly or Trp.

Another preferred tetrapeptide of the present invention is Pro-Ile-Gly-Trp (SEQ ID NO:3).

The formula for the especially preferred pentapeptides, hexapeptides and heptapeptides, which are also disclosed throughout this specification, may be:

$$R^1\text{-Phe-Pro}^1\text{-AA}^2\text{-Gly-AA}_{(n)}\text{-AA}^3\text{-NH}_2,$$

wherein $R^1$ is preferably a halogen atom, preferably a fluorine or chlorine atom, a carboxyl group, an amino group or a nitro group, with all modifications preferably at the C4 atom of Phe; $Pro^1$ is 3,4-dehydro Pro, Homo-Pro, cis- or trans-4OH-Pro or Pro, as listed in order of preference, $AA^2$ is preferably Arg, Ile, Leu or His, with Arg being especially preferred; $AA_{(n)}$ is 0–2 amino acid residues, if n=1, then Gly is preferred and if n=2, then Ile-Gly, Ile-Ile or Gly-Gly is preferred; $AA^3$ is preferably Trp or Gly, with Trp most preferred.

The present invention further provides admixtures of the peptides of formula (1) through formula (11) with known antidepressant compounds such as amitriptyline, fluoxetine (Prozac) and sertraline (Zoloft). It is within the ordinary skill of the artisan to generate various admixtures with the peptides of the present invention beyond the exemplifications disclosed throughout this specification.

The peptides with which this invention is concerned are readily prepared by conventional procedures (i.e., carbodiimide method, mixed anhydride method, N, N-carbonyldiimidazole method) for the step-wise synthesis of polypeptides, and also including solid phase peptide synthesis. The substituent groups are also readily added to the polypeptide residues by conventional procedures.

While it is not intended that the present invention be bound by any particular theory or mechanism, it is believed that certain of the peptides disclosed herein function to treat physiological, psychosomatic, neurological and/or psychiatric disorders at least in part by binding to serotonin receptors and to neuropeptide Y receptors in the brain of a patient to whom the peptides are administered. For example, experimental work has shown that the compounds having the formula 4-F-Phe- trans-4-OH-Pro-Arg-Gly-Trp-NH$_2$ (SEQ ID NO:43), following subcutaneous administration to rats, are found at detectable levels and substantially unchaged in the hippocampus and the amygdala, which are known to be sites of receptors including 5-HT and neuropeptide Y receptors, and which receptors are known to be involved in depression and its treatment. Additional experimental work has shown that peptide compounds disclosed herein interact with the serotonin releaser d-fenfluramine, and may act as a 5-HT 2A antagonist, indicating that the mechanism of action of the peptide compounds involves the serotonergic pathway, in a different way from that of the SSRIs. While it is not intended that the present invention be bound by any particular theory, it is believed that certain of the peptides disclosed herein function to treat physiological, psychosomatic, neurological or psychiatric disorders in a patient by administering to the patient one or more peptide compounds that bind to at least one of 5-HT and neuropeptide Y receptors in the brain of the patient. The present invention further provides methods and compositions for treating physiological, psychosomatic, neurological or psychiatric disorders in a patient by administering to the patient one or more peptide compounds that involve in their mechanism of action, at least in part, the serotonergic and/or neuropetide Y-ergic pathway. In preferred embodiments, the peptide compounds that are acting, at least in part, via the serotenergic and/or neuropetide Y-ergic pathway are effective in treating anxiety. In highly preferred embodiments, the peptide compounds that are acting, at least in part, via the serotenergic and/or neuropetide Y-ergic pathway have a formula 4-F-Phe-cis- or trans-4-OH-Pro-Arg-Gly-Trp-NH$_2$ (SEQ ID NO:43).

The peptides of the invention possess antidepressant activity as determined by the Porsolt swim test. The procedure used is described in the Examples hereinbelow. The Porsolt swim test is based on the observation that when a rat is forced to swim in a situation from which there is no escape, the rat ceases to move altogether and makes only those movements necessary to keep its head above water. Immobility indicates a state of despair. Therefore, a compound with activity as an antidepressant will delay the onset of immobility.

Compositions disclosed herein may be administered in a variety of formulations, in which the peptides disclosed herein are the "active ingredient", and which may include other ingredients, as well as additives and processing aids known in the art. The active ingredient may be formulated in combination with such other agents as, for example, local anesthetics and therapeutic agents. The other agents may be mixed in the compositions and administered prior to, simultaneously with or subsequent to administration of the compositions provided for the methods herein.

The active ingredient, which may comprise one or more of the peptides disclosed herein, maybe formulated in a suitable pharmaceutical carrier for in vivo administration to the patient by any standard method known in the art. Appropriate routes of administration of the compositions include oral, sublingual, parenteral (e.g., intravenous, intraspinal, intrathecal, intraventricular, epidermal, intracisternal, intracutaneous or intradermal, subcutaneous, or intramuscular), epicutaneous or transdermal, intranasal, rectal or vaginal. The compositions may be formulated as injectables, as oral or rectal formulations for systemic administration; and for local and topical administration as creams, aqueous or nonaqueous suspension, lotions, emulsions, suspensions or emulsions containing micronized particles, gels, foams, aerosols, solids and other suitable vehicles for application to the skin, eyes, lips and mucosa; as suppositories or cream for vaginal administration, and as combinations with bandages, patches, bioadhesives and dressings.

Oral administration routes include capsules, solutions, suspensions, gels, powders, elixirs and syrups. Sublingual administration routes include tablets, solutions, suspensions, elixirs, syrups, and lozenges. Parenteral administration routes include solutions and suspensions. Epicutaneous or transdermal administration routes include, but are not necessarily limited to, ointments, creams, pastes, plasters, powders, aerosols, lotions, transdermal patches, discs and solutions. Intranasal administration routes include solutions, sprays, inhalants or ointments. Rectal administration routes include ointments and suppositories. The active ingredient may also be formulated for incorporation into liposomes, microcapsules, or into polymer or wax-based preparations, which may be for controlled release. Additional guidance regarding routes of administration and the generation of pharmaceutically effective dose rates may be found in "Dosage Form Design: Biopharmaceutical Considerations" in *Pharmaceutical Dosage Forms and Drug Delivery Systems*, Chapter 3, Ansel, H. C. and Popovich, N. G., Fifth Ed.; Lea and Febiger, Philadelphia (1990).

The concentration of the peptide(s) used in any of the aforementioned formulations will depend upon the effective dose and the mode of administration used to elicit the appropriate biological effect. The dose should be sufficient to achieve circulating plasma concentrations of the active ingredient such that effective amounts cross the blood-brain barrier that are efficacious. For example, when the tetrapeptide Pro-Leu-Gly-Trp-NH$_2$ (SEQ ID NO:5) is the active ingredient, a circulating plasma level from about 30 mg to about 90 mg per average adult may be used; preferably about 60 mg per average adult. Effective doses for various routes of administration may be extrapolated from dose-response curves derived from in vitro or animal model test systems.

The methods and compositions disclosed herein are useful in treating patients suffering from a variety of physiological, psychosomatic, neurological or psychiatric disorders. For example, the methods and compositions disclosed herein are useful in treating patients suffering from anxiety disorder, including anxiety engendered or exacerbated by the use of certain medications by the patient. Some patients exhibit anxiety when administered certain antidepressant medications, particularly SSRIs such as fluoxetine. The effects of some medications in causing or exacerbating anxiety are referred to as "anxiogenic effects". It has been found that peptides disclosed herein may reduce or alleviate anxiogenic effects of antidepressant medications such as fluoxetine. It has further been found that peptides disclosed herein can be used to treat anxiety in patients suffering from anxiety disorder, or anxiety disorder in conjunction with depression. Preferred peptides for use in treatment of anxiety include compounds disclosed herein and having formulas 4-F-Phe-cis- or trans-4-OH-Pro-Arg-Gly-Trp-NH$_2$ (SEQ ID NO:43).

The invention will be further clarified by a consideration of the following examples, which are intended to be purely exemplary of the synthesis and use of the peptides of the invention. Peptides disclosed herein provide antidepressant activity as measured in the Porsolt swim test. The Example Section contains data comparing exemplified peptides disclosed herein with known antidepressants amitriptyline, fluoxetine and sertraline generated in a series of Porsolt swim tests.

EXAMPLES

Example 1
Effectiveness of Peptide Compounds in Treating Anxiety

The effectiveness of peptide compounds in treating anxiety can be confirmed using tests performed on rats. The tests include a social interaction test and an elevated maze test. Detailed procedures for the tests are described in Gonzalez et al., "Selectively bred lines of rat differ in social interaction and hippocampal 5-HT1A receptor function: A link between anxiety and depression?", *Pharmacol. Biochem. Behav.* 59: 787–792 (1998); and File et al., "Chronic fluoexitine in tests of anxiety in rat lines selectively bred for differential 5-HT1A receptor function". *Pharmacol. Biochem. Behav.* 62: 695–701 (1999), the disclosures of which are herein incorporated by reference in their entirety.

Thirty-two rats are used in the tests, divided into groups of 8 to be used in 4 experiments. Flinders Sensitive Line (FSL) rats are used in these examples. FSL rats are genetically predisposed to be sensitive to antidepressive agents. They resemble depressed humans in that they have elevated REM sleep, appetite and weight changes, reduced activity, and increased anhedonia after exposure to stressors. FSL rats also exhibit exaggerated immobility in the Porsolt swim test, which is counteracted by both tricyclic antidepressants and serotonin reuptake inhibitors.

Group I is administered chronic doses of a pharmaceutically acceptable vehicle for injectable medication for 21 days, then a single injection of the vehicle alone 30 minutes prior to being submitted to a social interaction test. Group II is administered chronic doses of the vehicle alone for 21 days, then 5 mg/kg of fluoxetine 30 minutes prior to the social interaction test. Group III is administered 0.2 mg/kg of the compound being tested for 21 days, then a single injection of the vehicle alone prior to the social interaction test. Group IV is administered 0.2 mg/kg of the test compound for 21 days, then a single injection of 5 mg/kg of fluoxetine 30 minutes prior to the social interaction test.

For the social interaction test, the rats are placed into a square, open field, 2 ft×2 ft, with 16 squares marked out in the field. The rats are not familiar with the field, and low lighting conditions are imposed. Rats are paired on the basis of body weight and treatment conditions, and each pair is placed into the field for 5 minutes. Rats are observed, and scored on the basis of time spent in social interaction (e.g., grooming, sniffing, following), and the number of times each rat crosses a line by two forepaws.

The elevated maze test is conducted 2 to 9 minutes after the social interaction test. The maze is made of black perspex and comprises two opposing closed arms and two opposing open arms, with a central arena between the arms. The arms are elevated 50 cm from the ground, and the central arena is at ground level. The central arena measures 10×10 cm. Each rat being tested is placed separately in the maze with its head in the central arena. The rats are observed and measurements are taken of the number of entries into the closed arms of the maze by the entire rat (an indicator of activity) and time spent in the open arms of the maze by at least two forepaws (an indicator of anxiety).

Example 2
Measurement of Anxiolytic and Antidepressant Effects of Peptide Compounds This example tests whether chronic treatment with compounds known to have antidepressive effects also modifies social interaction behavior, thereby indicating whether the compounds have anxiolytic effects. Eighteen FSL rats are used. Ten rats are treated with 0.2 mg/kg of a test compound in an injection vehicle daily for 14 days. Eight rats are treated only with the injection vehicle. Approximately 22 hours after the last treatment, each rat is separately placed into a social action arena for 5 minutes. Line crossings by forepaws and social interaction are recorded.

Immediately following the social interaction test, each rate is subjected to the Porsolt swim test. Each rat is placed into a cylinder of 25° C. water for 5 minutes. Latency and swimming are recorded according to known procedures for the Porsolt test.

Other embodiments of the invention will be apparent to those persons skilled in the art from a consideration of this specification or practice of the invention disclosed herein. It is intended that the specification and examples be considered as exemplary only, with the true scope and spirit of the invention to which exclusive rights are claimed being assessed by the appended claims.

What is claimed is:

1. A method for treating a physiological, psychosomatic, neurological or psychiatric disorder in a patient, comprising administering to the patient at least one pentapeptide or salt thereof having a general formula (7b):

$$R^1\text{-}AA^1\text{-}R^2\text{-}Pro^1\text{-}AA^2\text{-}Gly\text{-}Trp\text{-}NH_2 \quad (7b)$$

wherein $Pro^1$ represents the amino acid Pro; $AA^1$ represents the amino acid Phe: $AA^2$ represents an amino acid selected from the group consisting of D-Leu and Arg; and $R^1$ and $R^2$ each independently are selected from the group consisting of a hydrogen atom, a lower alkyl group having 1 to 3 carbon atoms, at least one halogen atom, a hydroxyl group, a sulphydryl group, an alkylamino group, a diakylamino group, and a cyano group wherein said disorder is selected from the group consisting of bipolar disorder, seasonal affective disorder, bulimia, anorexia nervosa, exogenous obesity, chronic fatigue syndrome, fibromyalgia, sexual dysfunction, anxiety disorder, attention deficit disorder, Parkinson's disease, schizophrenia, jet lag syndrome and addiction disorders.

2. A method for treating a physiological, psychosomatic, neurological or psychiatric disorder in a patient, comprising administering to the patient at least one pentapeptide or salt thereof having a general formula (7b):

$$R^1\text{-}AA^1\text{-}R^2\text{-}Pro^1\text{-}AA^2\text{-}Gly\text{-}Trp\text{-}NH_1 \quad (7b)$$

wherein $Pro^1$ represents the amino acid Pro; $AA^1$ represents the amino acid Phe: $AA^2$ represents an amino acid selected from the group consisting of D-Leu and Arg; and $R^1$ and $R^2$ each independently are selected from the group consisting of a hydrogen atom, a lower alkyl group having 1 to 3 carbon atoms, at least one halogen atom, a hydroxyl group, a sulphydryl group, an alkylamino group, a diakylamino group, and a cyano group wherein said disorder is alcohol dependency.

3. A method for treating a physiological, psychosomatic, neurological or psychiatric disorder in a patient, comprising administering to the patient at least one pentapeptide or salt thereof having a general formula (7b):

$$R^1\text{-}AA^1\text{-}R^2\text{-}Pro^1\text{-}AA^2\text{-}Gly\text{-}Trp\text{-}NH_2 \quad (7b)$$

wherein $Pro^1$ represents the amino acid Pro; $AA^1$ represents the amino acid Phe; $AA^2$ represents an amino acid selected from the group consisting of D-Leu and Arg; and $R^1$ and $R^2$ each independently are selected from the group consisting of a hydrogen atom, a lower alkyl group having 1 to 3 carbon atoms, at least one halogen atom, a hydroxyl group, a sulphydryl group, an alkylamino group, a diakylamino group, and a cyano group wherein said disorder is refractory depression.

4. A method for treating a physiological, psychosomatic, neurological or psychiatric disorder in a patient, comprising administering to the patient at least one pentapeptide or salt thereof having a general formula (7b):

$$R^1\text{-}AA^1\text{-}R^2\text{-}Pro^1\text{-}AA^2\text{-}Gly\text{-}Trp\text{-}NH_2 \quad (7b)$$

wherein $Pro^1$ represents the amino acid Pro; $AA^1$ represents the amino acid Phe; $AA^2$ represents an amino acid selected from the group consisting of D-Leu and Arg; and $R^1$ and $R^2$ each independently are selected from the group consisting of a hydrogen atom, a lower alkyl group having 1 to 3 carbon atoms, at least one halogen atom, a hydroxyl group, a sulphydryl group, an alkylamino group, a diakylamino group, and a cyano group wherein said disorder is a psychosomatic disorder.

5. A method for treating a physiological, psychosomatic, neurological or psychiatric disorder in a patient, comprising administering to the patient at least one pentapeptide or salt thereof having a general formula (7b):

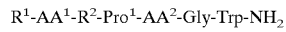    (7b)

wherein $Pro^1$ represents the amino acid Pro; $AA^1$ represents the amino acid Phe; $AA^2$ represents an amino acid selected from the group consisting of D-Leu and Arg; and $R^1$ and $R^2$ each independently are selected from the group consisting of a hydrogen atom, a lower alkyl group having 1 to 3 carbon atoms, at least one halogen atom, a hydroxyl group, a sulphydryl group, an alkylamino group, a diakylamino group, and a cyano group wherein said disorder is anxiety.

6. The method of claim 5, wherein said anxiety is accompanied by depression.

* * * * *